United States Patent

Henning et al.

[11] Patent Number: 5,010,057
[45] Date of Patent: Apr. 23, 1991

[54] RENIN-INHIBITING PEPTIDES HAVING AN AMINOMETHYL SIDE CHAIN

[75] Inventors: Rolf Henning, Wuppertal; Günter Benz, Velbert; Johannes-Peter Stasch, Wuppertal; Andreas Knorr, Erkrath; Wolfgang Bender, Wuppertal all of Fed. Rep. of Germany

[73] Assignee: Bayer Aktiengesellschaft, Leverkusen, Fed. Rep. of Germany

[21] Appl. No.: 395,392

[22] Filed: Aug. 17, 1989

[30] Foreign Application Priority Data

Aug. 27, 1988 [DE] Fed. Rep. of Germany ....... 3829086
Jan. 30, 1989 [DE] Fed. Rep. of Germany ....... 3902615

[51] Int. Cl.$^5$ ............................................. A61K 37/02
[52] U.S. Cl. ...................................... 514/018; 530/330
[58] Field of Search ................... 514/18, 58.4, 45, 19, 514/17; 530/330, 331, 332

[56] References Cited

U.S. PATENT DOCUMENTS

| | | | |
|---|---|---|---|
| 4,609,641 | 9/1986 | Evans et al. | 514/19 |
| 4,725,584 | 2/1988 | Luly et al. | 514/19 |
| 4,812,442 | 3/1989 | Boger et al. | 514/18 |
| 4,818,748 | 4/1989 | Bender et al. | 514/18 |
| 4,845,079 | 7/1989 | Luly et al. | 514/18 |

OTHER PUBLICATIONS

Burger, *Medicinal Chemistry*, 1960, pp. 565-571, 578-581, 600-601.
Plattner et al., J. Med. Chem., 1988, 31(12), 2277-2288.
Denkewalter et al., *Progress In Drug Research*, vol. 10, 1966, pp. 510-512.
Lehninger, *Biochemistry*, pp. 197-201, 1970.
Kempf et al., "Renin Inhibitors Based on . . . ", *Journal of Med. Chem.*, Nov. 1987, pp. 1978-1983.

Primary Examiner—Lester L. Lee
Assistant Examiner—Stephen B. Maebius
Attorney, Agent, or Firm—Spring Horn Kramer & Woods

[57] ABSTRACT

Rein-inhibiting aminomethyl peptides of the formula

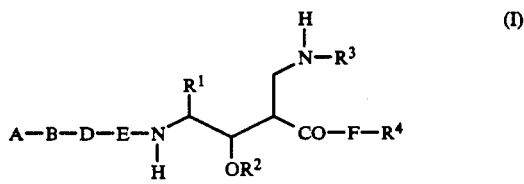

in which
A is H, an alkyl radical, a sulphonyl radical or an amino-protecting group,
B, D, E and F each independently is a direct bond or an amino-organo-carbonyl group,
$R^1$ is an optionally substituted alkyl or aryl radical,
$R^2$ is H, alkyl or acyl,
$R^3$ is H, alkyl, aryl or acyl, and
$R^4$ is alkyl, alkoxy, aryl or amino,
and physiologically acceptable salts thereof.

11 Claims, No Drawings

RENIN-INHIBITING PEPTIDES HAVING AN AMINOMETHYL SIDE CHAIN

The invention relates to new renin-inhibiting aminomethyl peptides, a process for their preparation and their use in medicaments, in particular in circulation-influencing medicaments.

Renin is a proteolytic enzyme which is predominantly produced by the kidneys and secreted in the plasma. It is known that renin cleaves the decapeptide angiotensin I from angiotensinogen in vivo. Angiotensin I is degraded, in turn, in the lungs, the kidneys or other tissues to the octapeptide angiotensin II which affects blood pressure. The various effects of angiotensin II such as vasoconstriction, Na+ retention in the kidney, aldosterone release in the adrenal gland and an increase in tone of the sympathetic nervous system act synergistically in the sense of an increase in blood pressure.

The activity of the renin-angiotensin system can be pharmacologically manipulated by the inhibition of the activity of renin or the angiotensin converting enzyme (ACE) and also by blockade of angiotensin II receptors. The development of orally utilizable ACE inhibitors has therefore led to new antihypertensives (compare German Offenlegungsschrift 3,628,650, Am. J. Med. 77, 690, 1984).

A more recent tendency is to intervene in the renin-angiotensin cascade at an earlier point in time, namely by inhibiting the highly specific peptidase renin.

Hitherto, various types of renin inhibitors have been developed: renin-specific antibodies, phospholipids, peptides having the N-terminal sequence of prorenin, synthetic peptides as substrate analogues and modified peptides.

New renin inhibitors have now been found which are derived from the amino acid (3S, 4S)-4-amino-3-hydroxy-6-methylheptanecarboxylic acid (statin) (compare D. H. Rich, J. Med. Chem. 28, 263–73 (1985), Boger, J.; Lohr, N. S.; Ulm, E. H.; Poe, M. ; Blaine, E. H.; Fanelli, G. M.; Lin, T.-Y.; Payne, L. S.; Schorn, T. W.; LaMont, B. I.; Vassil, T. C.; Stabilito, I. I.; Veber, D. F.; Rich, D. H. Boparai, A. S., Nature (London) 1983, 303, 81.

Owing to the introduction of an aminomethyl side chain, in addition to high selectivity towards human renin they show high stability towards enzymatic degradation and good water solubility. The invention relates to aminomethyl peptides of the general formula (I)

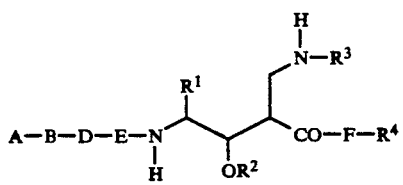

in which
A denotes hydrogen or
  represents $C_1-C_8$-alkyl, $C_1-C_8$-alkylsulphonyl, phenylsulphonyl or tolylsulphonyl or
  represents a group of the formula $COR^5$ or $COOR^6$
in which
$R^5$ represents straight-chain or branched alkyl having up to 10 carbon atoms, which is optionally substituted by hydroxyl, aryl, amino, alkylamino having up to 8 carbon atoms per alkyl group or dialkylamino having up to 8 carbon atoms per alkyl group
and
$R^6$ represents straight-chain or branched alkyl having up to 8 carbon atoms
or
A represents an amino-protecting group
B represents a direct bond or
  represents a group of the formula

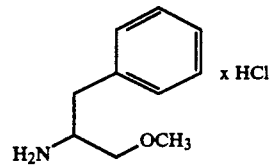

in which
p denotes a number 1, 2 or 3
m denotes a number 0, 1 or 2
n denotes a number 0, 1, 2, 3 or 4
$R^7$ denotes hydrogen, $C_1-C_8$-alkyl, hydroxymethyl, hydroxyethyl, carboxyl, $C_1-C_8$-alkoxycarbonyl or mercaptomethyl or
  represents a group of the formula —$CH_2$-NH-$R^8$ in which
$R^8$ represents hydrogen, $C_1-C_8$-alkyl, phenylsulphonyl, $C_1-C_8$-alkylsulphonyl or
  represents an amino-protecting group
$R^7$ denotes guanidinomethyl, methylthiomethyl, halogen, indolyl, imidazolyl, pyridyl, triazolyl or pyrazolyl which is optionally substituted by $R^8$, where
$R^8$ has the abovementioned meaning or
  represents cycloalkyl having 3 to 8 carbon atoms
  represents aryl which can be monosubstituted, disubstituted or trisubstituted by identical or different $C_1-C_6$-alkyl, $C_1-C_6$-alkoxy, $C_1-C_6$-alkylbenzyloxy, trifluoromethyl, halogen, hydroxyl or nitro, or by a group of the formula

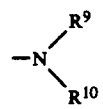

in which
$R^9$ and $R^{10}$ are identical or different and
  represent hydrogen, $C_1-C_8$-alkyl, $C_1-C_6$-alkylsulphonyl, aryl, aralkyl, tolylsulphonyl, acetyl, benzoyl or
  represent an amino-protecting group or
  represents a group of the formula

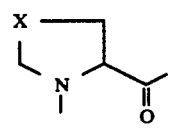

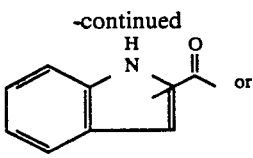
or

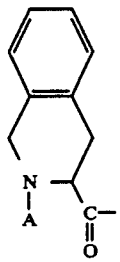

in which
X represents methylene, hydroxymethylene, ethylene, sulphur or oxygen, and
A has the abovementioned meaning
D has the abovementioned meaning of B and is identical or different to this,
E has the above mentioned meaning of B and is identical or different to this,
F has the abovementioned meaning of B and is identical or different to this,
$R^1$ represents straight-chain or branched alkyl having up to 10 carbon atoms which is optionally substituted by halogen, hydroxyl, cycloalkyl having 3 to 8 carbon atoms, amino, alkylamino having up to 8 carbon atoms, dialkylamino having up to 8 carbon atoms per alkyl group or phenyl which, in turn, may be substituted by $C_1$-$C_8$-alkyl, amino, nitro, cyano or halogen or
represents aryl having 6 to 10 carbon atoms which can be monosubstituted to tetrasubstituted by identical or different $C_1$-$C_6$-alkyl, $C_1$-$C_6$-alkoxy, hydroxyl, cyano, nitro, trifluoromethyl, trifluoromethoxy, trifluoromethylthio or phenyl, or by the group of the formula

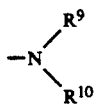

in which
$R^9$ and $R^{10}$ are identical or different and have the abovementioned meaning,
$R^2$ denotes hydrogen or
represents straight-chain or branched alkyl having up to 10 carbon atoms or
represents the group of the formula
$COR^5$
in which
$R^5$ has the abovementioned meaning,
$R^3$ denotes hydrogen or
represents straight-chain or branched alkyl having up to 10 carbon atoms which may be substituted by halogen, hydroxyl, aryl, aralkyl or heteroaryl or
represents a group of the formula

—$COR^5$ in which
$R^5$ has the abovementioned meaning
$R^3$ represents aryl which may be monosubstituted to tetrasubstituted by identical or different halogen, hydroxyl, nitro, cyano, $C_1$-$C_8$-alkoxy, $C_1$-$C_8$-alkyl or amino
$R^4$ represents straight-chain or branched alkyl having up to 10 carbon which is optionally substituted by hydroxyl, cycloalkyl having 3 to 8 carbon atoms, halogen, $C_1$-$C_8$-alkoxy, $C_1$-$C_8$-alkoxycarbonyl or aryl or
represents $C_1$-$C_8$-alkoxy or
represents aryl which may be monosubstituted, disubstituted or trisubstituted by identical or different halogen, hydroxyl, nitro, cyano, amino or $C_1$-$C_8$-alkoxy or
represents a radical

—HN—$R^{11}$ in which
$R^{11}$ denotes hydrogen or
represents straight-chain or branched alkyl having up to 10 carbon atoms which is optionally substituted by hydroxyl, halogen, $C_1$-$C_8$-alkoxy, $C_1$-$C_8$-alkoxycarbonyl, cycloalkyl having 3 to 8 carbon atoms, aryl or heteroaryl or
represents cycloalkyl having 3 to 8 carbon atoms or
represents phenyl which may be substituted by hydroxyl, halogen, nitro, cyano, $C_1$-$C_8$-alkyl, $C_1$-$C_8$-alkoxycarbonyl or by amino,
and their physiologically acceptable salts.

Amino-protecting group within the context of the invention repreents the amino-protecting groups customarily employed in peptide chemistry.

These preferably include: benzyloxycarbonyl, 4-bromobenzyloxycarbonyl, 2-chlorobenzyloxycarbonyl, 3-chlorobenzyloxycarbonyl, dichlorobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, 3,4,5-trimethoxybenzyloxycarbonyl, methoxycarbonyl, ethoxycarbonyl, propopoxycarbonyl, isopropoxycarbonyl, butoxycarbonyl, isobutoxycarbonyl, tert-butoxycarbonyl, pentoxycarbonyl, isopentoxycarbonyl, hexoxycarbonyl, cyclohexoxycarbonyl, octoxycarbonyl, 2-ethylhexoxycarbonyl, 2-iodohexoxycarbonyl, 2-bromoethoxycarbonyl, 2-chloroethoxycarbonyl, 2,2,2-trichloroethoxycarbonyl, 2,2,2-trichloro-tert-butoxycarbonyl, benzhydryloxycarbonyl, bis-(4-methoxyphenyl)methoxycarbonyl, phenacyloxycarbonyl, 2-trimethylsilylethoxycarbonyl, 2-(di-n-butyl-methylsilyl)ethoxycarbonyl, 2-triphenylsilylethoxycarbonyl, 2-(dimethyl-tert-butylsilyl)ethoxycarbonyl, menthyloxycarbonyl, vinyloxycarbonyl, allyloxycarbonyl, phenoxycarbonyl, tolyloxycarbonyl, 2,4-dinitrophenoxycarbonyl, 4-nitrophenoxycarbonyl, 2,4,5-trichlorophenoxycarbonyl, naphthyloxycarbonyl, fluorenyl-9-methoxycarbonyl, ethylthiocarbonyl, methylthiocarbonyl, butylthiocarbonyl, tert.-butylthiocarbonyl, phenylthiocarbonyl, benzylthiocarbonyl, methylaminocarbonyl, ethylaminocarbonyl, methylthiocarbonyl, butylthiocarbonyl, tert-butylthiocarbonyl, phenylthiocarbonyl, benzylthiocarbonyl, methylaminocarbonyl, ethylaminocarbonyl, propylaminocarbonyl, iso-propylaminocarbonyl, formyl, acetyl, propionyl, pivaloyl, 2-chloroacetyl, 2-bromoacetyl, 2-iodoacetyl, 2,2,2-trifluoroacetyl, 2,2,2-trichloroacetyl, benzoyl, 4-chlorobenzoyl, 4-methoxybenzoyl, 4-nitrobenzyl, 4-nitrobenzoyl, naphthylcarbonyl, phenoxyacetyl, adamantylcarbonyl, dicyclohexylphosphoryl, diphenylphosphoryl, dibenzylphosphoryl, di-(4-nitrobenzyl)phosphoryl, phenoxyphenylphosphoryl, diethylphosphinyl, diphenylphosphinyl, phthaloyl or phthalimido.

Particularly preferred amino-protecting groups are benzyloxycarbonyl, 3,4-dimethoxybenzyloxycarbonyl, 3,5-dimethoxybenzyloxycarbonyl, 4-methoxybenzyloxycarbonyl, 4-nitrobenzyloxycarbonyl, 2-nitrobenzyloxycarbonyl, 3,4,5-trimethoxybenzyloxycarbonyl, methoxycarbonyl, ethoxycarbonyl, propoxycarbonyl, iso-propoxycarbonyl, butoxycarbonyl, isobutoxycarbonyl, tert-butoxycarbonyl, cyclohexoxycarbonyl, hexoxycarbonyl, octoxycarbonyl, 2-bromoethoxycarbonyl, 2-chloroethoxycarbonyl, phenoxyacetyl, naphthylcarbonyl, adamantylcarbonyl, phthaloyl, 2,2,2-trichloroethoxycarbonyl, 2,2,2-trichloro-tert-butoxycarbonyl, menthyloxycarbonyl, vinyloxycarbonyl, allyloxycarbonyl, phenoxycarbonyl, 4-nitrophenoxycarbonyl, fluoroenyl-9-methoxycarbonyl, formyl, acetyl, propionyl, pivaloyl, 2-chloroacetyl, 2-bromoacetyl, 2,2,2-trifluoroacetyl, 2,2,2-trichloroacetyl, benzoyl, 4-chlorobenzoyl, 4-bromobenzoyl, 4-nitrobenzoyl, phthalimido or isovaleroyl.

The compounds of the general formula (I) according to the invention have several asymmetric carbon atoms. They can be present independently of one another in the D- or L-form. The invention includes the optical antipodes as well as the isomeric mixtures or racemates.

Preferably, the groups B, D, E and F are present independently of one another in the optically pure form, preferably in the L-form.

The group of the formula

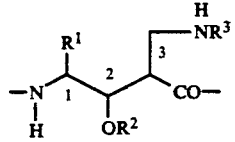

may possess, independently of the definition of the radicals, up to 3 asymmetric carbon atoms which can be present independently of one another in the R- or S-configuration. Preferably, this group is in the 1S, 2S, 3R-configuration, 1R, 2S, 3R-configuration, 1S, 2R, 3S-configuration or in the 1R, 2R, 3S-configuration.

The 1S, 2S, 3R-configuration and the 1S, 2R, 3S-configuration are particularly preferred.

The compounds of the general formula (I) according to the invention may be present in the form of their salts. These may be salts of the compounds according to the invention with inorganic or organic acids or bases. The acid addition products preferably include salts with hydrochloric acid, hydrobromic acid, hydriodic acid, sulphuric acid, phosphoric acid or with carboxylic acids such as acetic acid, propionic acid, oxalic acid, glycolic acid, succinic acid, maleic acid, hydroxymaleic acid, methylmaleic acid, fumaric acid, adipic acid, malic acid, tartaric acid, citric acid, benzoic acid, cinnamic acid, lactic acid, ascorbic acid, salicylic acid, 2-acetoxybenzoic acid, nicotinic acid, isonicotinic acid, or sulphonic acids such as methanesulphonic acid, ethanesulphonic acid, benzenesulphonic acid, toluenesulphonic acid, naphthalene-2-sulphonic acid or naphthalenedisulphonic acid.

Preferred compounds of the general formula (I) are those in which

A denotes hydrogen or
represents $C_1$-$C_6$-alkyl, $C_1$-$C_6$-alkylsulphonyl, phenylsulphonyl or tolylsulphonyl or
represents a group of the formula $COR^5$ or $COOR^6$ in which
$R^5$ represents straight-chain or branched alkyl having up to 8 carbon atoms which is optionally substituted by hydroxyl, phenyl, amino, alkylamino having up to 6 carbon atoms or dialkylamino having up to 6 carbon atoms per alkyl group
and
$R^6$ represents straight-chain or branched alkyl having up to 6 carbon atoms
or
A represents an amino-protecting group
B represents a direct bond or
represents a radical of the formula

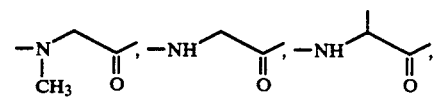

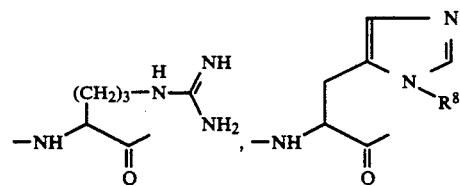

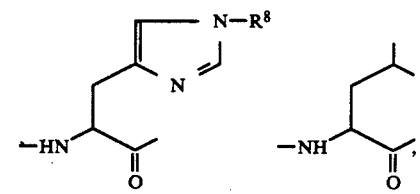

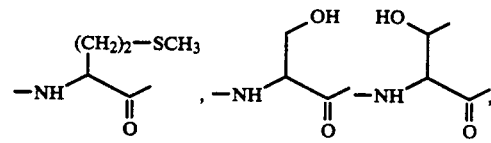

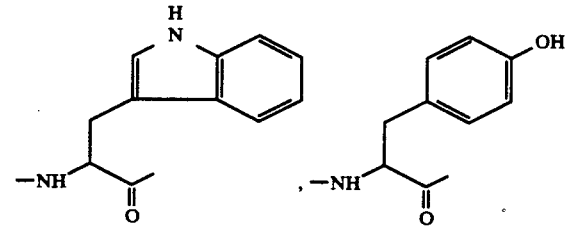

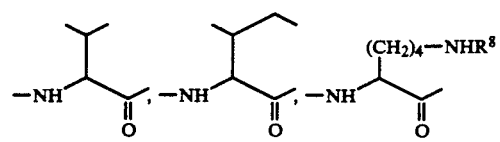

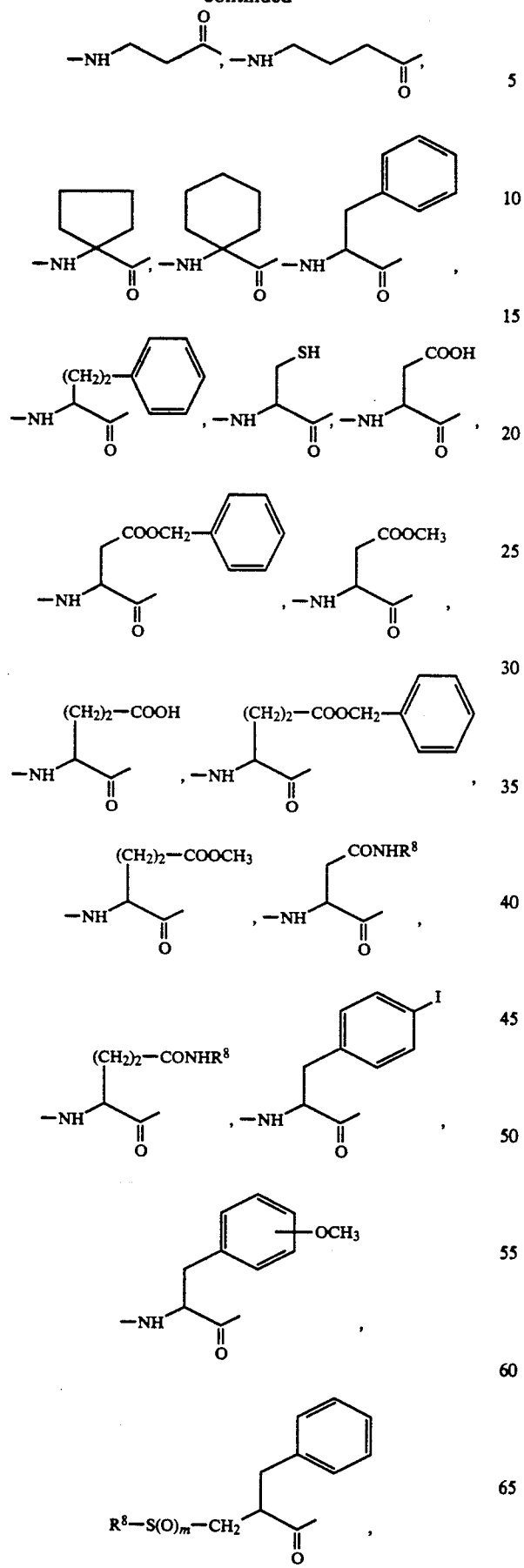
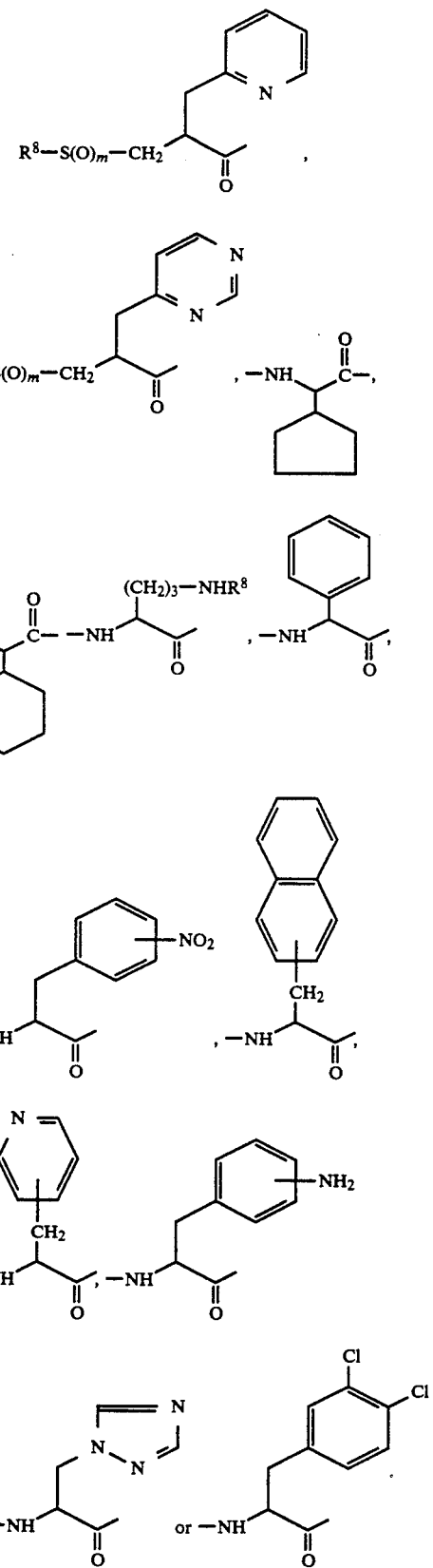
in their D-form, L-form or as the D,L-isomer mixture, preferably in the L-form, in which
m denotes a number 0, 1 or 2

$R^8$
denotes hydrogen or
represents $C_1$–$C_6$-alkyl, phenylsulphonyl, $C_1$–$C_4$-alkylsulphonyl or
represents an amino-protecting group,
represents a group of the formula

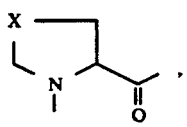,

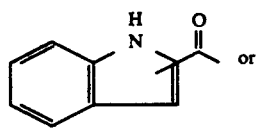 or

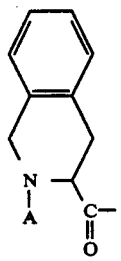

in which
X denotes methylene, sulphur or oxygen and
A has the abovementioned meaning
in their L-form, D-form or as the D,L-isomer mixture,
D, E and F are identical or different and have the same meaning as B and are identical or different to this
$R^1$ represents straight-chain or branched alkyl having up to 8 carbon atoms which is optionally substituted by fluorine, chlorine, bromine, hydroxyl, cycloalkyl having 3 to 8 carbon atoms, amino, alkylamino having up to 6 carbon atoms, dialkylamino having up to 6 carbon atoms per alkyl group or phenyl which, in turn, may be substituted by $C_1$–$C_6$-alkyl, amino, nitro, cyano or halogen or
represents phenyl which may be monosubstituted, disubstituted or trisubstituted by identical or different $C_1$–$C_4$-alkyl, $C_1$–$C_4$-alkoxy, hydroxyl, cyano, nitro, trifluoromethyl, trifluoromethoxy, trifluoromethylthio or phenyl, or by a group of the formula

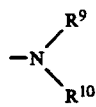

in which
$R^9$ and $R^{10}$ are identical or different and
represent hydrogen, $C_1$–$C_6$-alkyl, $C_1$–$C_4$-alkylsulphonyl, phenyl, benzyl, tolylsulphonyl, acetyl or benzoyl or
denote an amino-protecting group,
$R^2$ denotes hydrogen, or
represents straight-chain or branched alkyl having up to 8 carbon atoms or
represents the group of the formula $COR^5$,
in which $R^5$ has the abovementioned meaning,
denotes hydrogen or
represents straight-chain or branched alkyl having up to 8 carbon atoms which may be substituted by fluorine, chlorine, bromine, hydroxyl, phenyl, benzyl, pyridyl or pyrimidyl or
represents a group of the formula $COR^5$,
in which
$R^5$ has the abovementioned meaning or
represents phenyl which may be monosubstituted, disubstituted or trisubstituted by identical or different fluorine, chlorine, bromine, hydroxyl, nitro, cyano, $C_1$–$C_4$-alkoxy, $C_1$–$C_4$-alkyl or amino
$R^4$ represents straight-chain or branched alkyl having up to 8 carbon atoms which is optionally substituted by hydroxyl, cyclopropyl, cyclopentyl, cyclohexyl, fluorine, chlorine, bromine, $C_1$–$C_6$-alkoxy, $C_1$–$C_6$-alkoxycarbonyl or phenyl or
represents $C_1$–$C_6$-alkoxy or
represents phenyl which may be monosubstituted or disubstituted by identical or different fluorine, chlorine, bromine, hydroxyl, nitro, cyano, amino or $C_1$–$C_6$-alkoxy or
represents a radical $$-HN-R^{11}$$

in which
$R^{11}$ denotes hydrogen or
represents straight-chain or branched alkyl having up to 8 carbon atoms which is optionally substituted by hydroxyl, fluorine, chlorine, bromine, $C_1$–$C_6$-alkoxy, $C_1$–$C_6$-alkoxycarbonyl, cyclopropyl, cyclopentyl, cyclohexyl, phenyl, pyridyl or pyrimidyl or
represents cyclopropyl, cyclopentyl or cyclohexyl or
represents phenyl which may be substituted by hydroxyl, fluorine, chlorine, bromine, nitro, cyano, $C_1$–$C_6$-alkyl, $C_1$–$C_6$-alkoxycarbonyl or by amino,
and their physiologically acceptable salts.
Particularly preferred compounds of the general formula (I) are those in which
A denotes hydrogen or
represents $C_1$–$C_4$-alkyl, $C_1$–$C_4$-alkylsulphonyl, phenylsulphonyl or tolylsulphonyl or
represents a group of the formula $$-COR^5 \text{ or } -COOR^6$$

in which
$R^5$ represents straight-chain or branched alkyl having up to 6 carbon atoms which is optionally substituted by hydroxyl, phenyl, amino, alkylamino having up to 4 carbon atoms or by dialkylamino having up to 4 carbon atoms per alkyl group
$R^6$ represents straight-chain or branched alkyl having up to 4 carbon atoms or
A represents an amino-protecting group,
B represents a direct bond or
represents glycyl (Gly), alanyl (Ala), arginyl (Arg), histidyl (His), leucyl (Leu), isoleucyl (Ile), seryl (Ser), threonyl (Thr), tryptophyl (Trp), tyrosyl (Tyr), valyl (Val), lysyl (Lys), asparagyl (Asp), asparaginamido (Asn), glutamyl (Glu), glutaminamido (Gln), cystyl (Cys), methionyl (Met), phenylalanyl (Phe), 2-, 3- or 4-nitrophenylalanyl, 2-, 3- or 4-aminophenylalanyl or pyridylalanyl, optionally having an amino-protecting group, or prolyl (Pro), where the protein groups may in each case be present in their L-form or D-form or represents a group of the formula

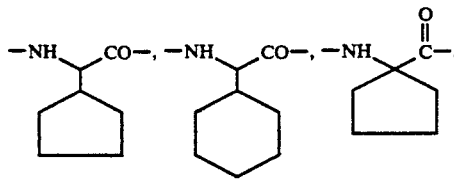

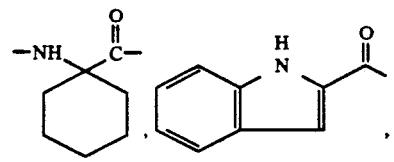

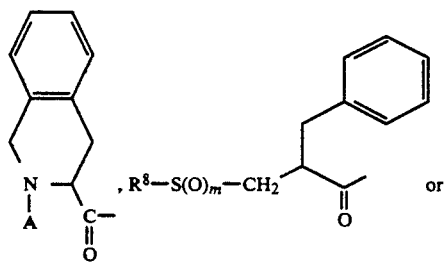

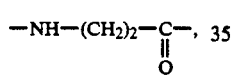

in which
A has the abovementioned meaning and $R^8$ represents $C_1-C_4$-alkyl

D, E and F are identical or different and have the same meaning as B and are identical or different to this, $R^1$ represents straight-chain or branched alkyl having up to 6 carbon atoms which is optionally substituted by fluorine, chlorine, hydroxyl, cyclopropyl, cyclopentyl, cyclohexyl, amino, alkylamino having up to 4 carbon atoms, dialkylamino having up to 4 carbon atoms per alkyl group, or phenyl which, in turn, may be substituted by $C_1-C_3$-alkyl, amino, nitro, cyano, fluorine or chlorine or represents phenyl which may be monosubstituted or disubstituted by identical or different $C_1-C_3$-alkyl, $C_1-C_2$-alkoxy, hydroxyl, cyano, nitro trifluoromethyl, trifluoromethoxy, trifluoromethylthio or phenyl, or by a group of the formula

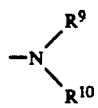

in which
$R^9$ and $R^{10}$ are identical or different and represent hydrogen, $C_1-C_3$-alkyl, $C_1-C_3$-alkylsulphonyl, phenyl, benzyl, tolylsulphonyl, acetyl or benzoyl or denote an amino-protecting group, $R^2$ denotes hydrogen or
represents straight-chain or branched alkyl having up to 6 carbon atoms or
represents the group of the formula $$-COR^5$$

in which
$R^5$ has the abovementioned meaning
denotes hydrogen or
represents straight-chain or branched alkyl having up to 6 carbon atoms which may be substituted by fluorine, chlorine, hydroxyl, phenyl, pyridyl or pyrimidyl or
represents a group of the formula $$-COR^5$$

in which
$R^5$ has the abovementioned meaning or
$R^3$ represents phenyl which may be monosubstituted or disubstituted by identical or different fluorine, chlorine, hydroxyl, nitro, cyano, $C_1-C_2$-alkoxy, $C_1-C_3$-alkyl or amino
$R^4$ represents straight-chain or branched alkyl having up to 6 carbon atoms which is optionally substituted by hydroxyl, cyclopropyl, cyclopentyl, cyclohexyl, fluorine, chlorine, $C_1-C_4$-alkoxy, $C_1-C_4$-alkoxycarbonyl or phenyl or
represents $C_1-C_4$-alkoxy or
represents phenyl which may be substituted by fluorine, chlorine, hydroxyl, nitro, cyano, amino or $C_1-C_4$-alkoxy or
represents a radical $$H-N-R^{11}$$

in which
$R^{11}$ denotes hydrogen or
represents straight-chain or branched alkyl having up to 6 carbon atoms which is optionally substituted by hydroxyl, fluorine, chlorine, bromine, $C_1-C_4$-alkoxy, $C_1-C_4$-alkoxycarbonyl, cyclopropyl, cyclopentyl, cyclohexyl, phenyl, pyridyl or pyrimidyl or
represents cyclopropyl, cyclopentyl or cyclohexyl or
represents phenyl which may be substituted by fluorine, chlorine, bromine, nitro, cyano, $C_1-C_3$-alkyl, $C_1-C_3$-alkoxycarbonyl or by amino, and their physiologically acceptable salts.

Salts of the compounds according to the invention having salt-forming groups may be prepared in a manner known per se, for example by reacting the compounds according to the invention containing acidic groups with corresponding bases or by reacting the compounds according to the invention containing basic groups with corresponding acids, in each case preferably with the abovementioned bases or acids.

Stereoisomer mixtures, in particular diastereomer mixtures, may be separated into the individual isomers in a manner known per se, for example by fractional crystallization or chromatography.

Racemates may be cleaved in a manner known per se, for example by converting the optical antipodes into diastereomers.

The compounds of the general formula (I) according to the invention

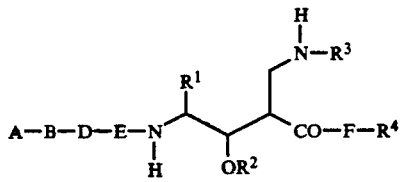 (I)

in which

A, B, D, E, F, $R^1$, $R^2$, $R^3$ and $R^4$ have the abovementioned meaning are obtained by first deblocking compounds of the general formula (II)

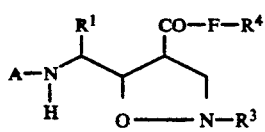 (II)

in which $R^1$, $R^3$, $R^4$, A and F have the abovementioned meanings by splitting off the group A by customary methods, and in a second step reacting with compounds of the general formula (III)

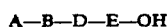 (III)

in which A, B, D and E have the abovementioned meanings, to give the compounds of the general formula (IIa)

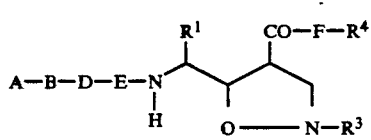 (IIa)

in which

A, B, D, E, F, $R^1$, $R^3$ and $R^4$ have the abovementioned meanings, and subsequently reducing the compounds of the general formula (IIa) by hydrogenolysis with ring opening.

The compounds of the general formula (II) are new and can be prepared by first hydrolyzing compounds of the general formula (IIb)

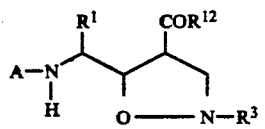 (IIb)

in which

A, $R^1$ and $R^3$ have the abovementioned meanings and $R^{12}$ represents $C_1$–$C_4$-alkoxy, according to customary methods and subsequently reacting with compounds of the general formula (IV)

 (IV)

in which

F and $R^4$ have the abovementioned meanings,

The compounds of the general formula (IIb) are new and can be prepared by reacting compounds of the general formula (V)

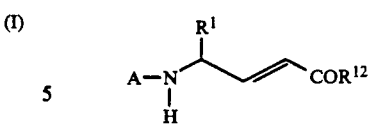 (V)

in which

A, $R^1$ and $R^{12}$ have the abovementioned meanings, with compounds of the general formula (VI)

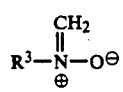 (VI)

in which $R^3$ has the abovementioned meaning, in a nitron cycloaddition reaction.

The synthesis can be illustrated by way of example by the following equation.

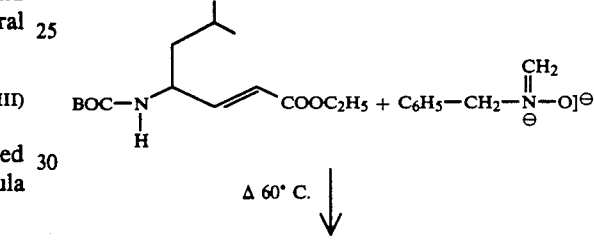

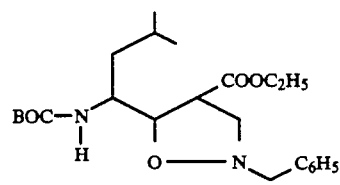

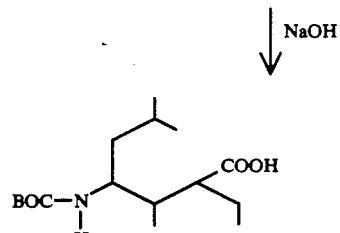

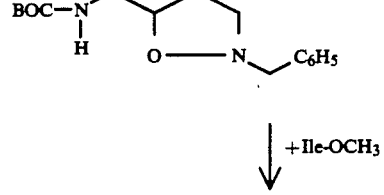

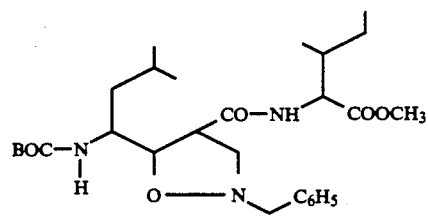

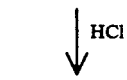

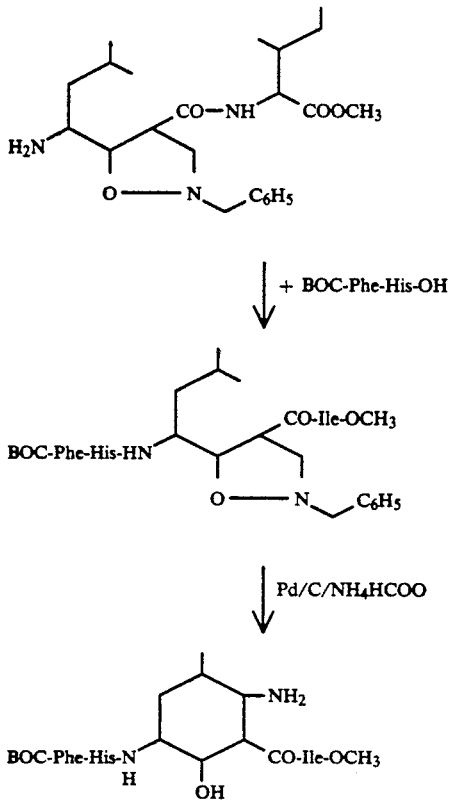

Suitable solvents for the additions of the compounds of the general formula (III) and (IV) are the customary inert solvents which do not change under the reaction conditions selected in each case. These include water or organic solvents such as diethyl ether, glycol monomethyl or dimethyl ether, dioxane or tetrahydrofuran, or hydrocarbons such as benzene, toluene, xylene, cyclohexane or mineral oil fractions or halogenated hydrocarbons such as methylene chloride, chloroform, carbon tetrachloride or acetone, dimethyl sulphoxide, dimethylformamide, hexamethylphosphoramide, ethyl acetate, pyridine, triethylamine or picoline.

Similarly, it is possible to use mixtures of the solvents mentioned.

Tetrahydrofuran, methylene chloride, dimethylformamide and ethyl acetate are preferred.

Customarily, the process is carried out in the presence of suitable solvents or diluents, optionally in the presence of an auxiliary or catalyst in a temperature range from −80° C. to 300° C., preferably from −30° C. to +30° C. at atmospheric pressure. Similarly, it is possible to work at elevated or reduced pressure.

Condensing agents which may also be bases are preferred as auxiliaries, in particular if the carboxyl group is activated as anhydride. The customary condensing agents such as carbodiimide, for example N,N'-diethyl-, N,N'-dipropyl-, N,N'-diisopropyl- or N,N'-dicyclohexylcarbodiimide, N-(3-dimethylaminoisopropyl)-N'-ethylcarbodiimide hydrochloride, or carbonyl compounds such as carbonyldiimidazole, or 1,2-oxazolium compounds such as 2-ethyl-5-phenyl-1,2-oxazolium 3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or benzotriazolyloxy-tris(dimethylamino)phosphonium hexafluorophosphate are preferably employed here and, as bases, alkali metal carbonates, for example the carbonate or hydrogencarbonate of sodium or potassium, or organic bases such as trialkylamines, for example triethylamine, N-ethylmorpholine or N-methylpiperidine.

The compounds of the general formula (III) can be prepared by reaction of an appropriate fragment, consisting of one or more amino acid groups, containing a free carboxyl group which is optionally in activated form with a complementary fragment, consisting of one or more amino acid groups containing an amino group which is optionally in activated form, and optionally repeating this procedure with appropriate fragments until the desired peptides of the general formula (III) have been prepared, and subsequently optionally splitting off protecting groups or exchanging for other protecting groups.

In this connection, additional reactive groups, such as for example amino or hydroxyl groups in the side chains of the fragments can optionally be protected by customary protecting groups.

Activated carboxyl groups are preferred in this connection:

Carboxylic acid azides (obtainable, for example, by reacting protected or unprotected carboxylic acid hydrazides with nitrous acid, its salts or alkyl nitrites (for example isoamyl nitrite), or unsaturated esters, in particular vinyl esters, (obtainable, for example, by reacting an appropriate ester with vinyl acetate), carbamoylvinyl esters (obtainable, for example, by reacting an appropriate acid with an isoxazolium reagent), alkoxyvinyl esters (obtainable, for example, by reacting the corresponding acids with alkoxyacetylenes, preferably ethoxyacetylene), or amidino esters, for example N,N'- or N,N-disubstituted amidino esters (obtainable, for example by reacting the appropriate acid with an N,N'-disubstituted carbodiimide (preferably dicyclohexylcarbodiimide, diisopropylcarbodiimide or N-(3-dimethylaminopropyl)-N'-ethylcarbodiimide hydrochloride) or with an N,N-disubstituted cyanamide, or aryl esters, in particular by phenyl esters substituted by electron-withdrawing substituents, for example 4-nitrophenyl, 4-methylsulphonylphenyl, 2,4,5-trichlorophenyl, 2,3,4,5,6-pentachlorophenyl or 4-phenyldiazophenyl esters (obtainable, for example, by reacting the corresponding acid with an appropriately substituted phenol, optionally in the presence of a condensing agent such as, for example, N,N'-dicyclohexylcarbodiimide, diisopropylcarbodiimide, N-(3-dimethylaminopropyl)-N'-ethylcarbodiimide hydrochloride, isobutyl chloroformate, propanephosphonic anhydride or benzotriazolyloxytris(dimethylamino)phosphonium hexafluorophosphate), or cyanomethyl esters (obtainable, for example, by reacting the corresponding acid with chloroacetonitrile in the presence of a base), or thioesters, in particular nitrophenyl thioesters, (obtainable, for example, by reacting the corresponding acid with nitrothiophenols, optionally in the presence of condensing agents such as N,N'-dicyclohexylcarbodiimide, diisopropylcarbodiimide, N-(3-dimethylaminopropyl)-N'-ethylcarbodiimide hydrochloride, isobutyl chloroformate, propanephosphonic anhydride, benzotriazolyloxytris(dimethylamino)phosphonium hexafluorophosphate), or amino or amido esters (obtainable, for example, by reacting the corresponding acid with an N-hydroxyamino or N-hydroxyamido compound, in particular N-hydroxysuccinimide, N-hydroxypiperidine, N-hydroxyphthalimide, N-hydroxy-5-norbornene-2,3-dicarboximide or 1-hydroxybenzotriazole, optionally in the presence of condensing agents such as N,N'-dicyclohexylcarbodiimide, diisopropylcarbodiimide or N-(3-dimethylaminopropyl)-N'-ethylcarbodiimide hydrochloride, isobutyl chloroformate or N-propanephosphonic anhydride), or anhydrides of acids, preferably symmetrical or unsymmetrical anhydrides of the corresponding acids, in particular anhydrides with inorganic acids (obtainable, for example, by reacting the corresponding acid with thionyl chloride, phosphorus pentoxide or oxalyl chloride), or anhydrides with carbonic acid hemiderivatives, for example carbonic acid lower alkyl hemiesters (obtainable, for example, by reacting the corresponding acid with haloformic acid lower alkyl esters, for example methyl chloroformate, ethyl chloroformate, propyl chloroformate, isopropyl chloroformate, butyl chloroformate or isobutyl chloroformate or with 1-lower alkoxycarbonyl-2-lower alkoxy-1,2-dihydroquinoline, for example 1-methoxycarbonyl-2-ethoxy-1,2-dihydroquinoline), or anhydrides with dihalophospho acids (obtainable, for example, by reacting the corresponding acid with phosphorus oxychloride), or anhydrides with phospho acid derivatives or phosphorus acid derivatives, (for example propanephosphonic anhydride, H. Wissmann and H. J. Kleiner, Angew. Chem. Int. Ed. 19, 133 (1980)) or anhydrides with organic carboxylic acids (obtainable, for example, by reacting the corresponding acids with an optionally substituted lower alkane- or phenylalkanecarbonyl halide, in particular phenylacetyl, pivaloyl or trifluoroacetyl chloride), or anhydrides with organic sulphonic acids (obtainable, for example, by reacting an alkali metal salt of a corresponding acid with a sulphonyl halide, in particular methane-, ethane-, benzene- or toluenesulphonyl chloride), or symmetrical anhydrides (obtainable, for example, by condensation of corresponding acids, if appropriate in the presence of condensing agents such as N,N'-dicyclohexylcarbodiimide, diisopropylcarbodiimide, N-(3-dimethylaminopropyl)-N'-ethylcarbodiimide hydrochloride, isobutyl chloroformate, propanephosphonic anhydride or benzotriazolyloxy-tris(dimethylamino)phosphonium hexafluorophosphate.

Reactive cyclic amides are in particular amides with 5-membered heterocycles having two nitrogen atoms and optionally aromatic character, preferably amides with imidazoles or pyrazoles (obtainable, for example, by reacting the corresponding acids with N,N'-carbonyldiimidazole or—optionally in the presence of condensing agents such as, for example, N,N'-dicyclohexylcarbodiimide, N,N'-diisopropylcarbodiimide, N-(3-dimethylaminopropyl)-N'-ethylcarbodiimide hydrochloride, isobutyl chloroformate, propanephosphonic anhydride, benzotriazolyloxy-tris(dimethylamino)phosphonium hexafluorophosphate—with, for example, 3,5-dimethylpyrazole, 1,2,4-triazole or tetrazole.

The amino acids employed in the definition B, D, E and F and therefore also the compounds of the general formula (IV) are known per se or can be obtained by known methods or are naturally occurring amino acids (Houben-Weyl's "Methoden der organischen Chemie" ("Methods of organic chemistry"), volume XV/1 and 2).

The reduction can be carried out either using catalysts such as palladium hydroxide or palladium/carbon or via a catalytic transfer hydrogenation in a manner known per se (compare Tetrahedron 41, 3479 (1985), 3463 (1985), Synthesis 1987, 53).

The customary organic solvents which do not change under the reaction conditions are suitable for the nitron cycloaddition. These include ethers such as diethyl ether, dioxane, tetrahydrofuran, glycol diethyl ether or hydrocarbons such as benzene, toluene, xylene, mesitylene, or mineral oil fractions or n-butyl acetate. Benzene, toluene, xylene or mesitylene are preferred.

The reaction can be carried out in a temperature range from 0° C. to 200° C., preferably at 30° C. to 90° C. and at elevated or atmospheric pressure.

The compounds of the general formulae (V) and (VI) are known per se or can be prepared by customary methods. (Chem. Pharm. Bull. 30, 1921 (1982) J. J. Tufariello in 1,3-Dipolar Cycloaddition Chemistry, Vol. 2, ed. A. Padwa p. 83-168, John Wiley (1984), R. Huisgen, H. Seidel, J. Brüning, Chem. Ber. 102, 1102 (1969)).

The compounds according to the invention affect the circulation. They can therefore be employed in medicaments for the treatment of high blood pressure and cardiac insufficiency.

In vitro test

The inhibitory strength of the peptides according to the invention against endogenous renin from human plasma is determined in vitro. Pooled human plasma is obtained with the addition of ethylenediaminetetraacetic acid (EDTA) as an anticoagulant and stored at −20° C. The plasma renin activities (PRA) are determined as the rate of formation of angiotensin I from endogenous angiotensinogen and renin by incubation at 37° C. The reaction solution contains 150 $\mu$l of plasma, 3 $\mu$l of 6.6% strength 8-hydroxyquinoline sulphate solution, 3 $\mu$l of 10% strength dimercaprol solution and 144 $\mu$l of sodium phosphate buffer (0.2 M; 0.1% EDTA; pH 5.6) with or without the substances according to the invention in various concentrations. The angiotensin I formed per unit of time is determined using a radioimmunoassay (Sorin Biomedica, Italy). The percentage inhibition of the plasma renin activity is calculated by comparison of the substances claimed herein. The concentration range in which the substances claimed herein show a 50% inhibition of plasma renin activity is between $10^{-4}$ to $10^{-9}$ M.

USE EXAMPLES

| Example No. | % Inhibition | IC $_{50}$(M) |
|---|---|---|
| 31 | 31 | |
| 35 | 34 | |
| 39 | 67 | |
| 77 | 96 | $1.1 \times 10^{-5}$ |
| 79 | 95 | $2.5 \times 10^{-6}$ |
| 82 | 89 | $1.4 \times 10^{-6}$ |
| 84 | 100 | $9.2 \times 10^{-8}$ |
| 85 | 100 | $2.4 \times 10^{-7}$ |
| 86 | 92 | $9.0 \times 10^{-6}$ |
| 94 | 100 | $3.7 \times 10^{-6}$ |
| 96 | 100 | $1.0 \times 10^{-6}$ |
| 97 | 100 | $2.2 \times 10^{-8}$ |

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this connection, the therapeutically active compound should in each case be present in a concentration from about 0.5 to 90% by weight of the total mixture, i.e. in amounts which are sufficient in order to achieve the dosage range indicated.

The formulations are prepared, for example, by extending the active compounds with solvents and/or excipients, optionally using emulsifiers and/or dispersants, where, for example, in the case of the use of water as a diluent, organic solvents may optionally be used as auxiliary solvents.

Auxiliaries which may be mentioned, for example, are:

Water, non-toxic organic solvents, such as paraffins (for example mineral oil fractions), vegetable oils (for example groundnut/sesame oil), alcohols (for example: ethyl alcohol, glycerol), excipients, such as, for example, ground natural minerals (for example kaolins, aluminas, talc, chalk), ground synthetic minerals (for example highly disperse silica, silicates), sugars (for example sucrose, lactose and dextrose), emulsifiers (for example polyoxyethylene fatty acid esters, polyoxyethylene fatty alcohol ethers), dispersants (for example ligninsulphite waste liquors, methylcellulose, starch and polyvinylpyrrolidone) and lubricants (for example magnesium stearate, talc, stearic acid and sodium sulphate).

Administration is carried out in a customary manner, preferably orally or parenterally, in particular perlingually or intravenously. In the case of oral administration, tablets may, of course, contain additions, such as sodium citrate, calcium carbonate and dicalcium phosphate together with various additives, such as starch, preferably potato starch, gelatin and the like in addition to the excipients mentioned. Furthermore, lubricants, such as magnesium stearate, sodium lauryl sulphate and talc can additionally be used for tableting. In the case of aqueous suspensions, various flavor improvers or colorants may be added to the active compounds in addition to the abovementioned auxiliaries.

In the case of parenteral administration, solutions of the active compounds may be employed using suitable liquid excipients.

In general, it has proved advantageous on intravenous administration to administer amounts of about 0.001 to 1 mg/kg, preferably about 0.01 to 0.5 mg/kg of body weight to attain effective results, and on oral administration the dose is about 0.01 to 20 mg/kg, preferably 0.1 to 10 mg/kg of body weight.

In spite of this it may sometimes be necessary to deviate from the amounts mentioned, depending on the body weight of the experimental animal or on the manner of administration, but also for reasons of the animal species and its individual behavior towards the medicament or the manner of its formulation and the point in time or interval at which administration takes place. Thus, in some cases it may be sufficient to manage with less than the minimum amount previously mentioned, whereas in other cases the said upper limit must be exceeded. In the case of administration of larger amounts, it may be advisable to divide these into a number of individual doses over the day. The same dose range is intended for administration in human medicine. Accordingly, the above embodiments also apply in this case.

The following mobile phase systems were used:
(a) 10:1 methylene chloride/methanol
(b) 20:1 methylene chloride/methanol
(c) 40:1 methylene chloride/methanol
(d) 2:1 n-hexane/ether
(e) 9:1:0.1 methylene chloride/methanol/formic acid
(f) 20:1 chloroform/acetone
(g) 15:1 methylene chloride/methanol
(h) 20:1 chloroform/methanol
(i) 9:1:0.1 methylene chloride/methanol/conc. ammonia
(j) 1:1 n-hexane/ethyl acetate
(k) 30:1 methylene chloride/methanol

| Abbreviations: | |
|---|---|
| Leu | leucine |
| Boc | tert.-butyloxycarbonyl |
| Ile | Isoleucine |
| NEM | N-ethylmorpholine |
| HOBT | 1-hydroxy-1H-benzotriazole |
| DCC | dicyclohexylcarbodiimide |
| AMP | 2-aminomethylpyridine |
| Phe | phenylalanine |
| His | histidine |
| Pro | proline |
| CHxAla | 3-cyclohexylalanine |

The following exemplary embodiments of Tables 1 to 3 (Examples 1 to 76) show precursors and intermediates and the exemplary embodiments of Tables 4 to 6 (Examples 77 to 109) describe the compounds of the formula (I).

EXAMPLE 1

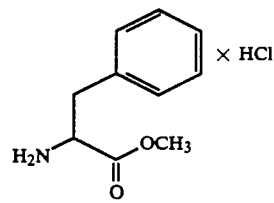

99 g (0.83 mol) of thionyl chloride were added dropwise to 600 ml of absolute methanol at −10° C. 100 g (0.605 mol) of L-phenylalanine were then introduced and the reaction mixture was heated under reflux for two hours. The solution was concentrated, the residue was dissolved in a just sufficient amount of absolute methanol and the product was precipitated by addition of absolute ether.

Yield: 119 g=91% of theory. m.p. 159° C.

EXAMPLE 2

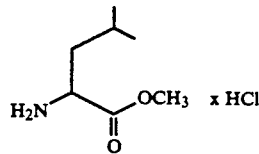

Example 2 is prepared analogously to the directions of Example 1.

Yield: 118.4 g=86% of theory. m.p. 148° C.

EXAMPLE 3

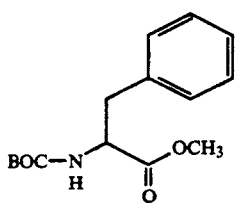

116 ml (0.834 mol) of triethylamine and 146 g (0.669 mol) of di-tert.-butyl pyrocarbonate were added successively at 5° C. to 119 g (0.553 mol) of the compound from Example 1 in 750 ml of DMF and the mixture was stirred overnight at room temperature. The mixture was filtered, the filtrate was concentrated, and the residue was taken up in 1:1 water/ethyl acetate and adjusted to pH 3 with dilute hydrochloric acid. The aqueous phase was extracted three times using ethyl acetate, and the combined organic phases were washed twice with saturated sodium chloride solution, dried over sodium sulphate and concentrated.

Yield: 154 g=100% of theory.
$R_F$(i): 0.86.

EXAMPLE 4

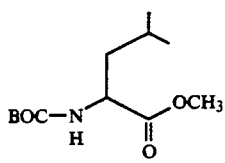

Example 4 is prepared analogously to the directions of Example 3.
Yield: 69 g=100% of theory.
$R_F$(a): 0.90.

EXAMPLE 5 tert.-Butoxycarbonyl-L-phenylalaninol

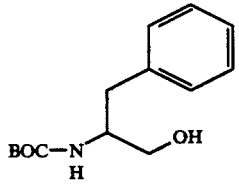

110.8 g (0.828 mol) of lithium iodide were added in portions to a suspension of 31.32 g (0.828 mol) of sodium borohydride in 200 ml of absolute tetrahydrofuran. A solution of 190.2 g (0.552 mol) of the compound from Example 3 in 320 ml of absolute tetrahydrofuran was then added dropwise and the suspension was stirred at 40° C. overnight. The mixture was cautiously poured into 10% strength citric acid solution, extracted four times using ethyl acetate, and the combined organic phases were washed twice with concentrated sodium chloride solution, dried over sodium sulphate and concentrated. The crude product was recrystallized from ethyl acetate/n-hexane.

Yield: 118 g=85% of theory.
m.p. 95° C.
$R_F$(a): 0.61.

EXAMPLE 6 tert.-Butoxycarbonyl-L-3-cyclohexylalaninol

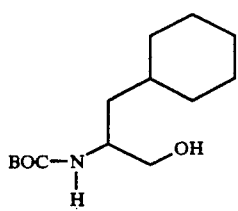

Example 6 is prepared analogously to the directions of Example 5.
Yield: 123.7 g=89% of theory.
$R_F$(b): 0.44.

EXAMPLE 7

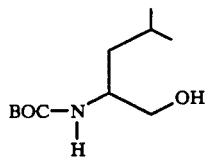

Example 7 is prepared analogously to the directions of Example 5.
Yield: 33.2 g=87.5% of theory.
$R_F$(b): 0.37.

EXAMPLE 8 tert.-Butoxycarbonyl-L-phenylalanianal

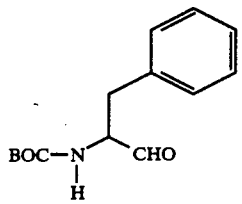

96 ml (0.69 mol) of triethylamine and 114 g (0.69 mol) of pyridine—SO3 complex were added to 57.9 g (0.23 mol) of Boc-phenylalaninol (Example 5) in 700 ml of DMSO with ice cooling and the mixture was stirred for one hour at room temperature. The solution was poured onto ice, extracted four times using ether, and the combined organic phases were washed twice with 10% strength citric acid, twice with 5% strength sodium hydrogencarbonate—and twice with half-saturated sodium chloride solution, dried over sodium sulphate and concentrated. The crude product was directly further processed.

Yield: 52.6 g=91.9% of theory.
$R_F$(a): 0.71.

EXAMPLE 9 tert.-Butoxycarbonyl-L-3-cyclohexylalaninal

-continued

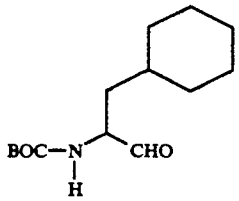

Example 9 is prepared analogously to the directions of Example 8.
Yield: 65 g=95% of theory.
$R_F$(b): 0.57.

EXAMPLE 10

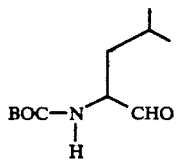

Example 10 is prepared analogously to the directions of Example 8.
Yield: 56 g=94% of theory.
$R_F$(a): 0.71.

EXAMPLE 11

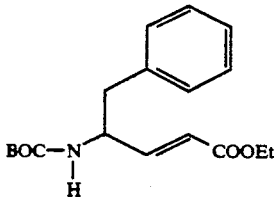

6.2 g (0.147 mol) of lithium chloride were added to a solution of 32.8 g (0.147 mol) of triethyl phosphonoacetate in 220 ml of absolute 1,2-dimethoxyethane and 18.0 g (0.140 mol) of diisopropylethylamine were then slowly added dropwise at 0° C. After stirring for 15 minutes at 0° C., a solution of 36.48 g (0.139 mol) of Boc-phenylalaninal (Example 8) in 200 ml of absolute 1,2-dimethoxyethane was added and the mixture was stirred for two days at room temperature. The resulting suspension was stirred into ice-cold 10% strength citric acid solution, extracted four times using ether, the combined organic phases were washed with saturated sodium chloride solution, dried over sodium sulphate and concentrated, and the crude product was filtered through silica gel in a column in 30:1 methylene chloride/methanol.
Yield: 36.3 g=77.6% of theory.
$R_F$(k): 0.67.

EXAMPLE 12

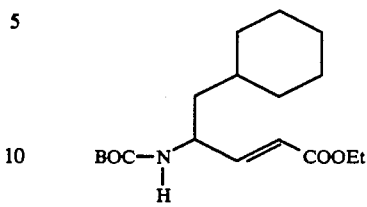

Example 12 is prepared analogously to the directions of Example 11.
Yield: 14.9 g=70.6% of theory, m.p.: 49°-50° C.
$R_F$(d): 0.39.

EXAMPLE 13

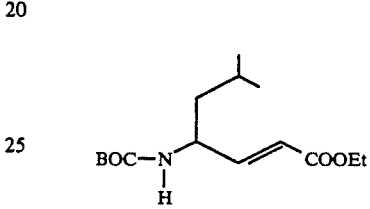

Example 13 is prepared analogously to the directions of Example 11.
Yield: 23 g=72.9% of theory of wax.
$R_F$(c): 0.58.

EXAMPLE 14

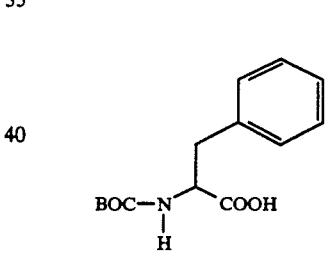

151 ml of 2 N sodium hydroxide solution and 88.7 g (0.366 mol) of 90% strength di-tert.-butyl pyrocarbonate were added to 50 g (0.30 mol) of L-phenylalanine in 900 ml of 2:1 dioxane/water. The mixture was stirred overnight at room temperature, then concentrated to about one third of the original volume, and the residue was diluted with water and extracted twice with ether at pH 9. The aqueous phase was acidified to pH 3 using dilute hydrochloric acid, extracted six times using ethyl acetate, and the combined ethyl acetate phases were washed with saturated sodium chloride solution, dried over sodium sulphate and concentrated. The residue was brought to crystallization by triturating with n-hexane and the product was filtered off with suction.
Yield: 77 g=95.5% of theory.
m.p. 84° C.

EXAMPLE 15 tert.-Butoxycarbonyl-L-3-cyclohexylalanine

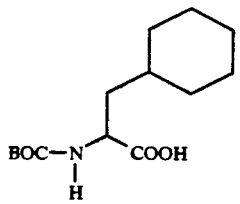

299 g (1.126 mol) of the compound from Example 14 in 1.1 l of methanol were hydrogenated at 30°–40° C. with 30 g of 5% strength Rh/C catalyst and a hydrogen pressure of 40–50 bar with the addition of 30 ml of glacial acetic acid. After the reaction had ended, the catalyst was filtered off and the solution was concentrated.

Yield: 306 g=100% of theory.

EXAMPLE 16 tert.-Butoxycarbonyl-L-3-cyclohexylalanine methyl ester

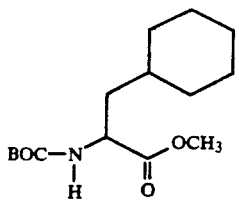

177.4 g (1.283 mol) of potassium carbonate and 56 ml (0.898 mol) of methyl iodide were added to 242.7 g (0.856 mol) of the compound from Example 15 in 1.2 l of DMF. After addition of a further 500 ml of DMF, the mixture was stirred vigorously at room temperature overnight, then filtered, the filtrate was concentrated and the residue was taken up in water and extracted four times using ether. The combined organic phases were washed with concentrated sodium chloride solution, dried over sodium sulphate and concentrated.

Yield: 232 g=95% of theory.
$R_F$(b): 0.82.

EXAMPLE 17 tert.-Butoxycarbonyl-L-isoleucine

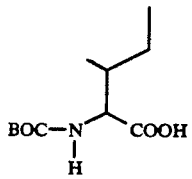

Example 17 is prepared analogously to the directions of Example 14.

Yield: 168.4 g=95.5% of theory.
m.p. 70° C.

EXAMPLE 18

N-Methylenebenzylamine-N-oxide

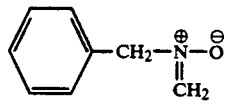

125 ml (1.585 mol) of 35% strength aqueous formaldehyde solution were added with intensive stirring to 65 g (0.313 mol) of N-benzylhydroxylamine in 630 ml of ether. The mixture was subsequently stirred for one further hour, then the organic phase was separated off, dried over sodium sulphate and concentrated. The crude product was directly further processed.

Yield: 65.7 g=92% of theory.

EXAMPLE 19

Ethyl 2-benzyl-5-(1-(S)-Boc-amino-2-phenylethyl)-isoxazolidine-4-carboxylate

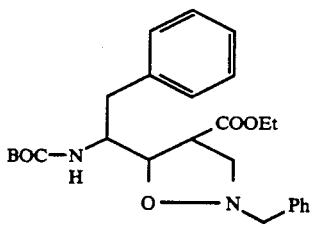

20 g (0.063 mol) of the compound from Example 11 and 16.9 g (0.125 mol) of the compound from Example 18 in 300 ml of toluene were stirred for 7 hours at 60° C. and then overnight at room temperature. After addition of a further 4.16 g (0.031 mol) of the compound from Example 18 in 25 ml of toluene, the mixture was once more heated to 60° C. for two hours, then the reaction mixture was washed twice with half-saturated sodium chloride solution, dried over sodium sulphate and concentrated. Column chromatography of the crude product on silica gel in 2:1 hexane/ether gave 12.65 g (44.5% of theory) of the non-polar and 4.26 g (15.0% of theory) of the polar isomer.

Total yield: 16.91 g=59.5% of theory.
$R_F$(d): 0.25 and 0.17.

EXAMPLE 20

Ethyl 2-benzyl-5-(1-(S)-Boc-amino-2-cyclohexylethyl)-isoxazolidine-4-carboxylate

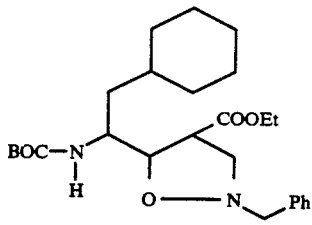

Example 20 is prepared analogously to the directions of Example 19.

Yield: 16.12 g=57% of theory.
$R_F$(d): 0.32 and 0.25.

EXAMPLE 21

Ethyl 2-benzyl-5-(1-(S)-Boc-amino-3-methylbutyl)-isoxazolidine-4-carboxylate

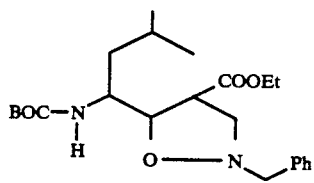

Example 21 is prepared analogously to the directions of Example 19.
Yield: 18.55 g=63.1% of theory.
$R_F$(d): 0.33 and 0.25.

EXAMPLE 22

2-Benzyl-5-(1-(S)-Boc-amino-3-methylbutyl)-isoxazolidine-4-carboxylic acid

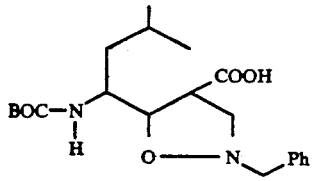

5.4 g (12.8 mmol) of the compound from Example 21 (isomer mixture) in 60 ml of 2:1 dioxane/water were stirred at room temperature for three hours with 14.1 ml of 1 N sodium hydroxide solution and then allowed to stand overnight in a refrigerator. The solution was concentrated to one third of the original volume, diluted with water and extracted twice with ether at pH 12. The aqueous phase was brought to pH 5 using dilute hydrochloric acid, extracted four times using ethyl acetate, and the combined ethyl acetate phases were washed with concentrated sodium chloride solution, dried over sodium sulphate and concentrated.
Yield: 4.75 g=94.4% of theory.
$R_F$(e): 0.45.

EXAMPLE 23

2-Benzyl-5-(1-(S)-Boc-amino-3-phenylethyl)-isoxazolidine-4-carboxylic acid

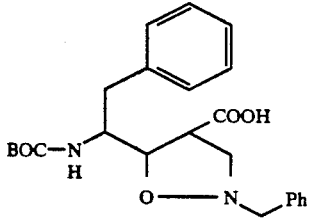

Example 23 is prepared analogously to the directions of Example 22.
Yield: 12.74 g=92.1% of theory.
$R_F$(e): 0.46.

EXAMPLE 24

2-Benzyl-5-(1-(S)-Boc-amino-2-cyclohexylethyl)-isoxazolidine-4-carboxylic acid

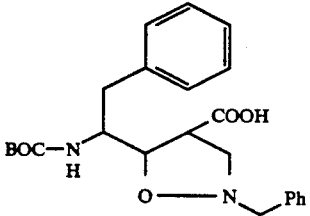

Example 24 is prepared analogously to the directions of Example 22.
Yield: 3.9 g=94% of theory.
$R_F$(e): 0.40 and 0.31.

EXAMPLE 25

Boc-L-isoleucine-2-aminomethylpyridyl amide

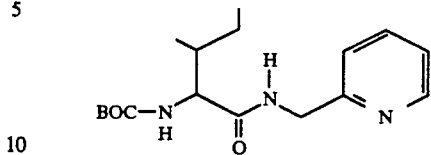

14.75 g (0.136 mol) of 2-picolylamine, 123 ml (0.886 mol) of triethylamine and 116 ml of a 50% strength solution of propanephosphonic anhydride in methylene chloride were added successively at 0° C. to 30 g (0.13 mol) of the compound from Example 17 in 250 ml of methylene chloride. The solution was stirred overnight at room temperature, then poured into ice-cold sodium hydrogencarbonate solution, the organic phase was washed once more with 5% strength sodium hydrogen carbonate and once more with saturated sodium chloride solution, dried over sodium sulphate and concentrated, and the crude product was filtered through silica gel in 15:1 methylene chloride/ methanol in a column.
Yield: 35.33 g=84.6% of theory.
$R_F$(g): 0.52.

EXAMPLE 26

L-Isoleucine-2-aminomethylpyridyl amide dihydrochloride

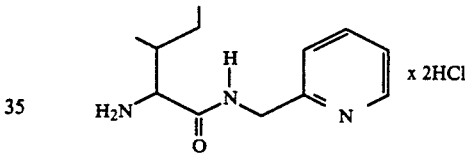

35.33 g (0.11 mol) of the compound from Example 25 were stirred with 150 ml of 4 N HCl/dioxane and 40 ml of absolute methanol for 75 minutes at 0° C. and for three hours at room temperature. The solution was concentrated, absolute ether was added to the residue a number of times and the mixture was in each case concentrated again, and the product was dried in a high vacuum.
Yield: 33 g=100% of theory.

EXAMPLE 27

N-[2-Benzyl-5-(1-(S)-Boc-amino-2-phenylethyl)-isoxazolidine-4-carbonyl]-L-isoleucine methyl ester

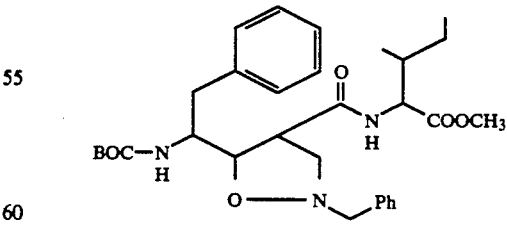

5.95 g (32.75 mmol) of L-Ile-OCH$_3$×HCl, 3.45 g (34.24 mmol) of triethylamine, 5.47 g (35.73 mmol) of HOBt and 7.06 g (34.24 mmol) of DCC were added successively at 0° C. to 12.7 g (29.77 mmol) of the compound from Example 23 (isomer mixture) in 100 ml of methylene chloride and the reaction mixture was stirred overnight at room temperature. The resulting precipitate was filtered off, and the filtrate was washed twice with 5% strength sodium hydrogen carbonate solution and once with saturated sodium chloride solution, dried over sodium sulphate and concentrated. The crude product was purified by column chromatography on silica gel in 40:1 methylene chloride/methanol.

Yield: 14 g=85% of theory.

$R_F$(c): 0.39 and 0.23.

The examples shown in Table 1 were prepared analogously to the directions of Example 27.

1.38 g (7.63 mmol) of L-Ile-OCH$_3$×HCl, 0.92 g (7.98 mmol) of N-ethylmorpholine, 1.27 g (8.32 mmol) of HOBt and 1.72 g (8.32 mmol) of DCC were added successively at 0° C. to 3.0 g (6.94 mmol) of the compound from Example 24 (isomer mixture) in 35 ml of methylene chloride and the reaction mixture was stirred overnight at room temperature. The resulting precipitate was filtered off, and the filtrate was washed twice with 5% strength sodium hydrogencarbonate solution and once with saturated sodium chloride solution, dried

TABLE 1

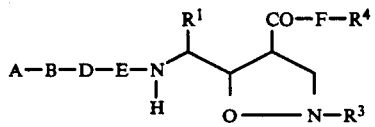

| Example No. | A | B | D | E | F | R$^1$ | R$^3$ | R$^4$ | R$_F$ |
|---|---|---|---|---|---|---|---|---|---|
| 28 | H | — | — | — | Ile | CH$_2$-C$_6$H$_5$ | CH$_2$—C$_6$H$_5$ | OCH$_3$ | 0.71 (i) |
| 29 | BOC | — | — | — | Ile | CH$_2$—C$_6$H$_5$ | CH$_2$—C$_6$H$_5$ | —NH—CH$_2$-(2-pyridyl) | 0.39 (h) |
| 30 | H | — | — | — | Ile | CH$_2$—C$_6$H$_5$ | CH$_2$—C$_6$H$_5$ | —NH—CH$_2$-(2-pyridyl) | 0.55 (i) |
| 31 | BOC | — | Phe | His | Ile | CH$_2$—C$_6$H$_5$ | CH$_2$—C$_6$H$_5$ | OCH$_3$ | 0.53 (a) |
| 32 | BOC | Pro | Phe | His | Ile | CH$_2$—C$_6$H$_5$ | CH$_2$—C$_6$H$_5$ | OCH$_3$ | 0.46 (a) |
| 33 | BOC | — | Phe | His | Ile | CH$_2$—C$_6$H$_5$ | CH$_2$—C$_6$H$_5$ | —NH—CH$_2$-(2-pyridyl) | 0.33 (i) |
| 34 | BOC | Pro | Phe | His | Ile | CH$_2$—C$_6$H$_5$ | CH$_2$—C$_6$H$_5$ | —NH—CH$_2$-(2-pyridyl) | 0.38 (i) |

EXAMPLE 35

N-[2-Benzyl-5-(1-(S)-Boc-amino-2-cyclohexylethyl)-isoxazolidine-4-carbonyl]-L-isoleucine methyl ester

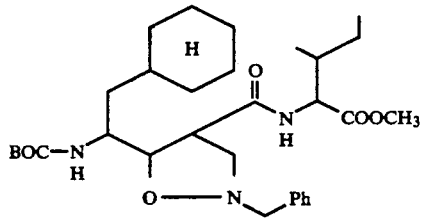

over sodium sulphate and concentrated. The crude product was purified by column chromatography on silica gel in 1:1 n-hexane/ethyl acetate.

Yield: 3.5 g=90% of theory.

$R_F$(j): 0.60 and 0.49.

The examples shown in Table 2 were prepared analogously to the directions of Example 35.

TABLE 2

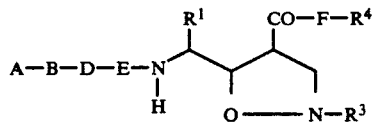

| Example No. | A | B | D | E | F | R$^1$ | R$^3$ | R$^4$ | R$_F$ |
|---|---|---|---|---|---|---|---|---|---|
| 36 | H | — | — | — | Ile | CH$_2$—C$_6$H$_{11}$ | CH$_2$—C$_6$H$_5$ | OCH$_3$ | |

TABLE 2-continued $$A-B-D-E-\underset{H}{N}-\overset{R^1}{\underset{O-N-R^3}{C}}H-CH-\overset{CO-F-R^4}{CH}$$

| Example No. | A | B | D | E | F | R¹ | R³ | R⁴ | R_F |
|---|---|---|---|---|---|---|---|---|---|
| 37 | BOC | — | — | — | Ile | $CH_2-C_6H_{11}$ | $CH_2-C_6H_5$ | $-HN-CH_2-\text{(2-pyridyl)}$ | 0.44 and 0.31 (h) |
| 38 | H | — | — | — | Ile | $CH_2-C_6H_5$ | $CH_2-C_6H_5$ | $-HN-CH_2-\text{(2-pyridyl)}$ | 0.50 (i) |
| 39 | BOC | — | Phe | His | Ile | $CH_2-C_6H_{11}$ | $CH_2-C_6H_5$ | $OCH_3$ | 0.45 (a) |
| 40 | H | — | Phe | His | Ile | $CH_2-C_6H_{11}$ | $CH_2-C_6H_5$ | $OCH_3$ | |
| 41 | BOC | Pro | Phe | His | Ile | $CH_2-C_6H_{11}$ | $CH_2-C_6H_5$ | $OCH_3$ | 0.55 (b) |
| 42 | BOC | — | Phe | His | Ile | $CH_2-C_6H_{11}$ | $CH_2-C_6H_5$ | $-HN-CH_2-\text{(2-pyridyl)}$ | 0.54 (i) |
| 43 | BOC | Pro | Phe | His | Ile | $CH_2-C_6H_{11}$ | $CH_2-C_6H_5$ | $-HN-CH_2-\text{(2-pyridyl)}$ | 0.38 (i) |
| 44 | BOC | — | — | — | — | $CH_2-C_6H_{11}$ | $CH_2-C_6H_5$ | $NH-iC_4H_9$ | 0.39 and 0.31 (c) |
| 45 | H | — | — | — | — | $CH_2-C_6H_{11}$ | $CH_2-C_6H_5$ | $NH-iC_4H_9$ | |
| 46 | BOC | — | Phe | His | — | $CH_2-C_6H_{11}$ | $CH_2-C_6H_5$ | $NH-iC_4H_9$ | 0.48 (i) |
| 47 | BOC | — | — | — | — | $CH_2-C_6H_{11}$ | $CH_2-C_6H_5$ | $NH-C_2H_4-C_6H_5$ | 0.43 and 0.34 (c) |
| 48 | H | — | — | — | — | $CH_2-C_6H_{11}$ | $CH_2-C_6H_5$ | $NH-C_2H_4-C_6H_5$ | |
| 49 | BOC | — | Phe | His | — | $CH_2-C_6H_{11}$ | $CH_2-C_6H_5$ | $NH-C_2H_4-C_6H_5$ | 0.47 (i) |
| 50 | — | — | $\text{+}SO_2-CH_2-CH(CH_2C_6H_5)-CHO$ | $-NH-CH(cyclopentyl)-CO-$ | Ile | $CH_2-C_6H_{11}$ | $CH_2-C_6H_5$ | $NH-CH_2-\text{(2-pyridyl)}$ | 0.36 (b) |
| 51 | BOC | — | Phe | $-NH-CH(cyclopentyl)-CO-$ | Ile | $CH_2-C_6H_{11}$ | $CH_2-C_6H_5$ | $-HN-CH_2-\text{(2-pyridyl)}$ | 0.33 (b) |

TABLE 2-continued $$A-B-D-E-\underset{H}{N}-\underset{\underset{O---N-R^3}{|}}{\overset{R^1}{C}H}-CH-\overset{CO-F-R^4}{C}H_2$$

| Example No. | A | B | D | E | F | R¹ | R³ | R⁴ | R_F |
|---|---|---|---|---|---|---|---|---|---|
| 52 | BOC | — | H, cyclohexane-N-CO- | His | Ile | CH₂—C₆H₁₁ | CH₂—C₆H₅ | —HN—CH₂-(2-pyridyl) | 0.42 (i) |
| 53 | — | — | indole-2-CO- | Phe | Ile | CH₂—C₆H₁₁ | CH₂—C₆H₅ | —HN—CH₂-(2-pyridyl) | 0.38 (b) |
| 54 | — | — | +SO₂—CH₂—CH(CH₂Ph)—CO- | His | Ile | CH₂—C₆H₁₁ | CH₂—C₆H₅ | —HN—CH₂-(2-pyridyl) | 0.53 and 0.51 (i) |
| 55 | Boc | — | tetrahydroisoquinoline-CO- | His | Ile | CH₂—C₆H₁₁ | CH₂—C₆H₅ | —HN—CH₂-(2-pyridyl) | 0.50 (i) |

EXAMPLE 56

N-[2-Benzyl-5-(1-(S)-Boc-amino-3-methylbutyl)-isoxazolidine-4-carbonyl]-L-isoleucine methyl ester

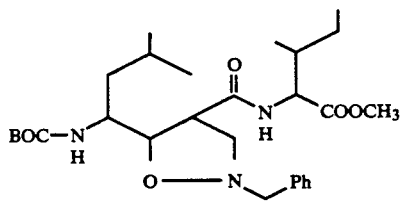

1.4 g (7.71 mmol) of L-Ile-OCH₃×HCl, 0.928 g (8.06 mmol) of N-ethylmorpholine, 1.29 g (8.41 mmol) of HOBt and 1.73 g (8.41 mmol) of DCC were added successively at 0° C. to 2.75 g (7.01 mmol) of the compound from Example 22 (isomer mixture) in 30 ml of methylene chloride and the reaction mixture was stirred overnight at room temperature. The resulting precipitate was filtered off, and the filtrate was washed twice with 5% strength sodium hydrogencarbonate solution and once with saturated sodium chloride solution, dried over sodium sulphate and concentrated. Column chromatography of the crude product on silica gel in 20:1 chloroform/acetone gave 1.83 g (50.3% of theory) of the non-polar and 1.11 g (30.5% of theory) of the polar isomer.

Total yield: 2.94 g=80.8% of theory.

R_F(f): 0.42 and 0.25.

The examples shown in Table 3 were prepared analogously to the directions of Example 56.

TABLE 3

| Example No. | A | B | D | E | F | R[1] | R[3] | R[4] | $R_F$ |
|---|---|---|---|---|---|---|---|---|---|
| 57 | H | — | — | — | Ile | iC4H9 | CH2—C6H5 | OCH3 | 0.47 (a) |
| 58 | BOC | — | — | — | Ile | iC4H9 | CH2—C6H5 | —HN—CH2-(2-pyridyl) | 0.47 (h)<br>0.37 (h) |
| 59 | H | — | — | — | Ile | iC4H9 | CH2—C6H5 | —HN—CH2-(2-pyridyl) | 0.31 (a) |
| 60 | BOC | — | Phe | His | Ile | iC4H9 | CH2—C6H5 | OCH3 | 0.46 (a) |
| 61 | H | — | Phe | His | Ile | iC4H9 | CH2—C6H5 | OCH3 | 0.23 (i) |
| 62 | BOC | Pro | Phe | His | Ile | iC4H9 | CH2—C6H5 | OCH3 | 0.45 (i) |
| 63 | BOC | — | Phe | His | Ile | iC4H9 | CH2—C6H5 | —HN—CH2-(2-pyridyl) | 0.43 (a)<br>0.32 (a) |
| 64 | BOC | Pro | Phe | His | Ile | iC4H9 | CH2—C6H5 | —HN—CH2-(2-pyridyl) | 0.26 (a)<br>0.17 (a) |
| 65 | Boc | — | — | (1-aminocyclohexanecarbonyl) | Ile | iC4H9 | CH2—C6H5 | —HN—CH2-(2-pyridyl) | 0.34 (b) |
| 66 | C2H5O—C(=O)— | — | Phe | His | Ile | iC4H9 | CH2—C6H5 | —HN—CH2-(2-pyridyl) | 0.38 (i) |

TABLE 3-continued $$A-B-D-E-\underset{H}{N}-\underset{R^1}{\overset{}{C}H}-CH(OH)-CH_2-CO-F-NH-R^4$$

| Example No. | A | B | D | E | F | R¹ | R³ | R⁴ | R_F |
|---|---|---|---|---|---|---|---|---|---|
| 67 | ⊢C(=O)– | — | Phe | His | Ile | iC₄H₉ | CH₂—C₆H₅ | —HN—CH₂-(2-pyridyl) | 0.33 (i) |
| 68 | Boc | — | (1,2,3,4-tetrahydroisoquinoline-3-carbonyl) | (cyclopentyl-acetyl-NH-) | Ile | iC₄H₉ | CH₂—C₆H₅ | —HN—CH₂-(2-pyridyl) | 0.33 (b) |
| 69 | — | — | ⊢SO₂—CH₂—CH(CH₂C₆H₅)—CO— | His | Ile | iC₄H₉ | CH₂—C₆H₅ | —HN—CH₂-(2-pyridyl) | 0.46 and 0.42 (i) |
| 70 | Boc | — | (1,2,3,4-tetrahydroisoquinoline-3-carbonyl) | His | Ile | iC₄H₉ | CH₂—C₆H₅ | —HN—CH₂-(2-pyridyl) | 0.49 (i) |

TABLE 3-continued $$A-B-D-E-N\underset{H}{-}\underset{\underset{O-N-R^3}{|}}{\overset{R^1}{C}}\overset{CO-F-R^4}{\underset{}{}}$$

| Example No. | A | B | D | E | F | $R^1$ | $R^3$ | $R^4$ | $R_F$ |
|---|---|---|---|---|---|---|---|---|---|
| 71 | Boc | — | cyclohexyl-C(=O)-NH- group | His | Ile | iC$_4$H$_9$ | CH$_2$—C$_6$H$_5$ | —HN—CH$_2$-(2-pyridyl) | 0.41 (i) |
| 72 | — | — | indole-CO- | Phe | Ile | iC$_4$H$_9$ | CH$_2$—C$_6$H$_5$ | —HN—CH$_2$-(2-pyridyl) | 0.32 and 0.28 (b) |
| 73 | — | — | — | indole-CH$_2$-CH(NH-)CO- | Ile | iC$_4$H$_9$ | CH$_2$—C$_6$H$_5$ | —HN—CH$_2$-(2-pyridyl) | 0.40 and 0.36 (b) |
| 74 | — | — | indole-CO- | —HN-CH$_2$-CH$_2$-CO— | Ile | iC$_4$H$_9$ | CH$_2$—C$_6$H$_5$ | —HN—CH$_2$-(2-pyridyl) | 0.23 and 0.18 (b) |
| 75 | — | — | indole-CO- | His | Ile | iC$_4$H$_9$ | CH$_2$—C$_6$H$_5$ | —HN—CH$_2$-(2-pyridyl) | 0.39 and 0.36 (i) |
| 76 | Boc | — | Phe | —HN-CH(cyclopentyl)-CO— | Ile | iC$_4$H$_9$ | CH$_2$—C$_6$H$_5$ | —HN—CH$_2$-(2-pyridyl) | 0.32 (b) |

EXAMPLE 77

N-[2-Aminomethyl-4-(S)-Boc-L-phenylalanyl-L-histidyl-amino-3-hydroxy-5-phenylpentanoyl]-L-isoleucine methyl ester

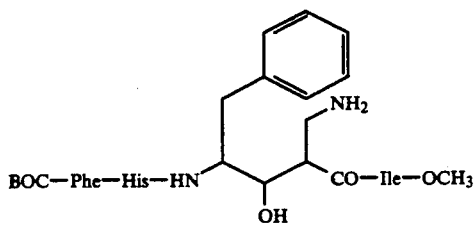

300 mg of 10% strength Pd/C catalyst were added to a solution of 500 mg (0.6 mmol) of the compound from Example 31 and 189 mg (3 mmol) of ammonium formate in 25 ml of methanol and the mixture was heated under argon for one hour under reflux. The catalyst was filtered off, the filtrate was concentrated, the residue was taken up in methylene chloride, washed once with half-saturated sodium chloride solution, dried over sodium sulphate and concentrated, and the crude product was purified by column chromatography on silica gel in 9:1:0.1 methylene chloride/methanol/conc. aqueous ammonia solution.

Yield: 380 mg = 84.7% of theory.
$R_F$(i): 0.17.

The examples shown in Table 4 were prepared analogously to the directions of Example 77.

14 μl (0.15 mmol) of acetic anhydride and 21 μl (0.15 mmol) of triethylamine were added at 0° C. to 110 mg (0.15 mmol) of the compound from Example 77 in 5 ml of methylene chloride and the mixture was stirred at 0° C. for 30 minutes. The solution was washed twice with saturated sodium chloride solution, dried over sodium sulphate and concentrated, and the crude product was purified by column chromatography on silica gel in 10:1 methylene chloride/methanol.

Yield: 88 mg = 74% of theory.
$R_F$(a): 0.27

EXAMPLE 82

N-[2-Aminomethyl-4-(S)-Boc-L-phenylalanyl-2-histidyl-amino-5-cyclohexyl-3-hydroxypentanoyl]-2-isoleucine methyl ester

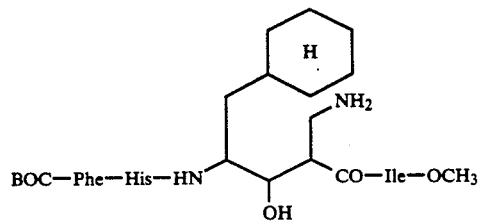

300 mg of 10% strength Pd/C catalyst were added to a solution of 500 mg (0.59 mmol) of the compound from Example 39 (non-polar isomer) and 186 mg (2.95 mmol) of ammonium formate in 20 ml of methanol and the mixture was heated under argon for one hour under

TABLE 4

$$A-B-D-E-\underset{H}{N}-\underset{\underset{OH}{|}}{\overset{\overset{R^1}{|}}{C}H}-CH-\underset{CO-F-R^4}{\overset{NH-R^3}{|}}$$

| Example No. | A | B | D | E | F | R¹ | R³ | R⁴ | $R_F$ |
|---|---|---|---|---|---|---|---|---|---|
| 78 | BOC | Pro | Phe | His | Ile | CH₂—C₆H₅ | H | OCH₃ | 0.28 and 0.21 (i) |
| 79 | BOC | — | Phe | His | Ile | CH₂—C₆H₅ | H | 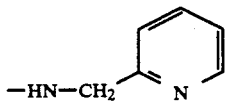 | 0.21 (i) |
| 80 | BOC | Pro | Phe | His | Ile | CH₂—C₆H₅ | H | 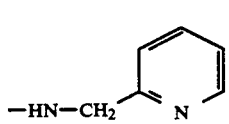 | 0.28 and 0.19 (i) |

EXAMPLE 81

N-[2-Acetamidomethyl-4-(S)-Boc-L-phenylalanyl-L-histidyl-amino-3-hydroxy-5-phenylpentanoyl]-L-isoleucine methyl ester

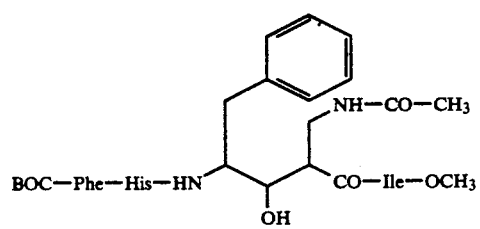

reflux. The catalyst was filtered off, the filtrate was concentrated, the residue was taken up in methylene chloride, washed once with halfsaturated sodium chloride solution, dried over sodium sulphate and concentrated, and the crude product was purified by column chromatography on silica gel in 9:1:0.1 methylene choride/methanol/conc. aqueous ammonia solution.

Yield: 259 mg = 58% of theory.
$R_F$(i): 0.12 and 0.09.

The examples shown in Table 5 were prepared analogously to the directions of Example 82.

TABLE 5

$$A-B-D-E-\underset{H}{N}-\overset{R^1}{\underset{OH}{C}}-\overset{NH-R^3}{\underset{CO-F-R^4}{C}}$$

| Example No. | A | B | D | E | F | R¹ | R³ | R⁴ | $R_f$ |
|---|---|---|---|---|---|---|---|---|---|
| 83 | BOC | Pro | Phe | His | Ile | $CH_2-C_6H_{11}$ | H | $OCH_3$ | 0.14 (i) |
| 84 | BOC | — | Phe | His | Ile | $CH_2-C_6H_{11}$ | H | 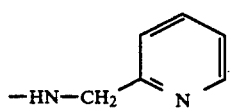 | 0.26 (i) |
| 85 | BOC | Pro | Phe | His | Ile | $CH_2-C_6H_{11}$ | H | 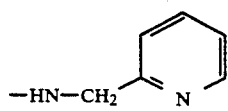 | 0.25 (i) |
| 86 | BOC | — | Phe | His | — | $CH_2-C_6H_{11}$ | H | $-NH\text{-}iC_4H_9$ | 0.13 (i) |
| 87 | BOC | — | Phe | His | — | $CH_2-C_6H_{11}$ | H | $-NH-C_2H_4-C_6H_5$ | 0.14 (i) |
| 88 | — | — | 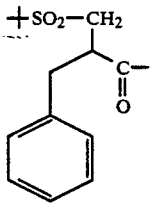 | 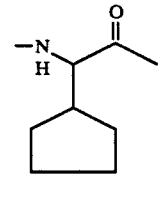 | Ile | $CH_2-C_6H_{11}$ | H | 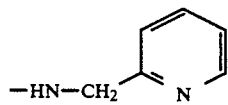 | 0.48 and 0.41 (i) |
| 89 | Boc | — | Phe | 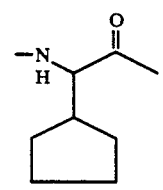 | Ile | $CH_2-C_6H_{11}$ | H | 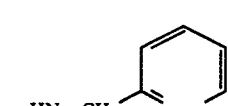 | 0.49 (i) |
| 90 | Boc | — | 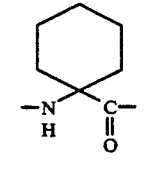 | His | Ile | $CH_2C_6H_{11}$ | H | 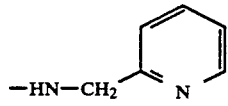 | 0.23 (i) |
| 91 | — | — | 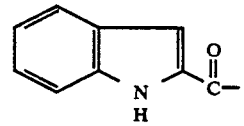 | Phe | Ile | $CH_2-C_6H_{11}$ | H | 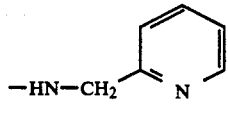 | 0.53 and 0.39 (i) |
| 92 | — | — | 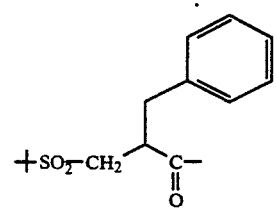 | His | Ile | $CH_2-C_6H_{11}$ | H | 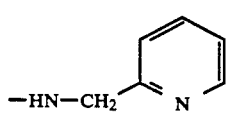 | 0.29 and 0.16 (i) |

TABLE 5-continued

A—B—D—E—N(H)—C(R¹)(H)—CH(OH)—CH(CH₂—NH—R³)—CO—F—R⁴

| Example No. | A | B | D | E | F | R¹ | R³ | R⁴ | R_f |
|---|---|---|---|---|---|---|---|---|---|
| 93 | Boc | — | (2-(1,2,3,4-tetrahydroisoquinolinyl)carbonyl group) | | His | Ile | CH₂—C₆H₁₁ | H | —HN—CH₂—(2-pyridyl) | 0.20 (i) |

EXAMPLE 94

N-[2-Aminomethyl-4-(S)-Boc-L-phenylalanyl-L-histidyl-amino-3-hydroxy-6-methylheptanoyl]-L-isoleucine methyl ester

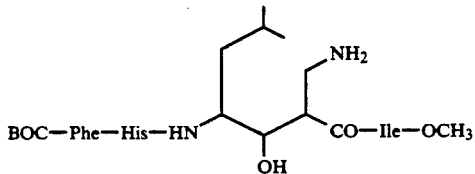

300 mg of 10% strength Pd/C catalyst were added to a solution of 500 mg (0.62 mmol) of the compound from Example 60 (non-polar isomer) and 196 mg (3.1 mmol) of ammonium formate in 20 ml of methanol and the mixture was heated under argon for one hour under reflux. The catalyst was filtered off, the filtrate was concentrated, the residue was taken up in methylene chloride, washed with half-concentrated sodium chloride solution, dried over sodium sulphate and concentrated, and the crude product was purified by column chromatography on silica gel in 9:1:0.1 methylene chloride/methanol/conc. aqueous ammonia solution.

Yield: 336 mg = 75.7% of theory (lyophilisate).

R_F (i): 0.20.

The examples shown in Table 6 were prepared analogously to the directions of Example 94.

TABLE 6

A—B—D—E—N(H)—CH(R¹)—CH(OH)—CH(NH—R³)—CO—F—R⁴ (structure shown at top)

| Example No. | A | B | D | E | F | R¹ | R³ | R⁴ | R_F |
|---|---|---|---|---|---|---|---|---|---|
| 95 | BOC | Pro | Phe | His | Ile | iC₄H₉ | H | OCH₃ | 0.21 and 0.16 (i) |
| 96 | BOC | — | Phe | His | Ile | iC₄H₉ | H | —HN—CH₂—(2-pyridyl) | 0.15 and 0.09 (i) |
| 97 | BOC | Pro | Phe | His | Ile | iC₄H₉ | H | —HN—CH₂—(2-pyridyl) | 0.13 and 0.09 (i) |
| 98 | (O=C+)⁻ | — | Phe | His | Ile | iC₄H₉ | H | —HN—CH₂—(2-pyridyl) | 0.17 and 0.08 (i) |
| 99 | — | — | (indolyl-acryloyl) | —N(CH₂)₂—C(=O)— | Ile | iC₄H₉ | H | —HN—CH₂—(2-pyridyl) | 0.20 and 0.17 (i) |
| 100 | — | — | (indolyl-acryloyl) | His | Ile | iC₄H₉ | H | —HN—CH₂—(2-pyridyl) | 0.14 and 0.08 (i) |

TABLE 6-continued

Structural formula:
A—B—D—E—N(H)—CH(R¹)—CH(OH)—CH(NH-R³)—CO—F—R⁴

| Example No. | A | B | D | E | F | R¹ | R³ | R⁴ | $R_F$ |
|---|---|---|---|---|---|---|---|---|---|
| 101 | BOC | — | tetrahydroisoquinoline-3-carbonyl | 1-cyclopentyl-2-oxopropylamino | Ile | iC₄H₉ | H | —HN—CH₂-(2-pyridyl) | 0.47 (i) |
| 102 | — | — | indole-CH=C(CO-)- | Phe | Ile | iC₄H₉ | H | —HN—CH₂-(2-pyridyl) | 0.40 and 0.29 (i) |
| 103 | BOC | — | Phe | 1-cyclopentyl-2-oxopropylamino | Ile | iC₄H₉ | H | —HN—CH₂-(2-pyridyl) | 0.43 (i) |
| 104 | BOC | 13 | — | 1-cyclohexyl-carbonylamino | Ile | iC₄H₉ | H | —HN—CH₂-(2-pyridyl) | 0.40 and 0.37 (i) |

TABLE 6-continued
Structure: A—B—D—E—F with R¹ on carbon α to N—H, NH—R³ on CH₂, CO—F—R⁴ with OH on adjacent carbon.
| Example No. | A | B | D | E | F | R¹ | R³ | R⁴ | R_F |
|---|---|---|---|---|---|---|---|---|---|
| 105 | — | — | — | 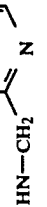 (2-acyl indole) | Ile | iC₄H₉ | H | —HN—CH₂—(2-pyridyl) | 0.39 (i) |
| 106 | C₂H₅—O—C(=O)— | — | Phe | His | Ile | iC₄H₉ | H | —HN—CH₂—(2-pyridyl) | 0.29 and 0.14 (i) |
| 107 | — | — |  (PhCH₂—CH(SO₂—CH₂—)—CO—) | His | Ile | iC₄H₉ | H | —HN—CH₂—(2-pyridyl) | 0.35 and 0.20 (i) |
| 108 | BOC | — |  | His | Ile | iC₄H₉ | H | —HN—CH₂—(2-pyridyl) | 0.29 (i) |
| 109 | BOC | — |  (1-amino-cyclohexane-CO—) | His | Ile | iC₄H₉ | H | —HN—CH₂—(2-pyridyl) | 0.40 (i) |

It is understood that the specification and examples are illustrative but not limitative of the present invention and that other embodiments within the spirit and scope of the invention will suggest themselves to those skilled in the art.

We claim:

1. An aminomethyl peptide of the formula

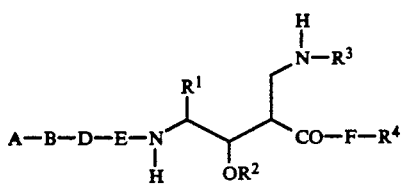
(I)

in which

A is selected from the group consisting of BOC, hydrogen and $C_2H_5-O-CO-$,

B is selected from the group consisting of Pro and a direct bond,

D is Phe or is

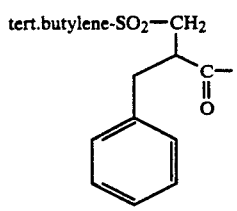

when A is hydrogen and B is a direct bond,

E is selected from the group consisting of His and

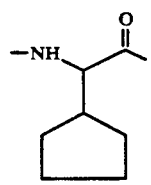

F is Ile, $R^1$ is alkyl with 1 to 4 carbon atoms optionally substituted by cyclohexyl or phenyl, $R^2$ and $R^3$ are each hydrogen and $R^4$ is selected from the group consisting of lower alkoxy and $NH-R^{11}$ wherein $R^{11}$ represents lower alkyl optionally substituted by pyridyl.

2. A compound according to claim 1, wherein such compound is N-[2-aminomethyl-4-Boc-phenylalanyl-histidylamino-3-hydroxy-5-phenylpentanoyl]-isoleucine N-(pyrid-2-yl-methyl)-amide of the formula

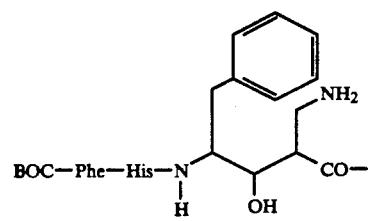

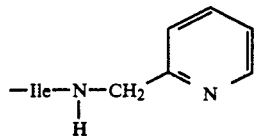

or a physiologically acceptable salt thereof.

3. A compound according to claim 1, wherein such compound is N-[2-aminomethyl-4-Boc-prolinyl-phenylalanylhistidyl-amino-3-hydroxy-5-phenylpentanoyl]-isoleucine N-(pyrid-2-yl-methyl)-amide of the formula

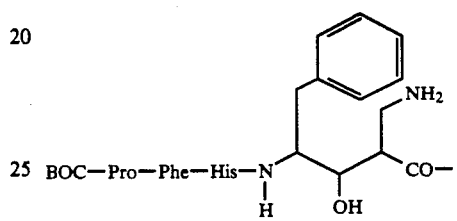

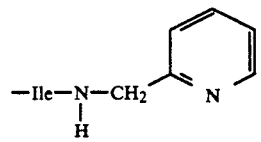

or a physiologically acceptable salt thereof.

4. A compound according to claim 1, wherein such compound is N-[2-aminomethyl-4-Boc-phenylalanyl-2-histidylamino-5-cyclohexyl-3-hydroxypentanoyl]-2-isoleucine N-(pyridyl-2-yl-methyl)-amide of the formula

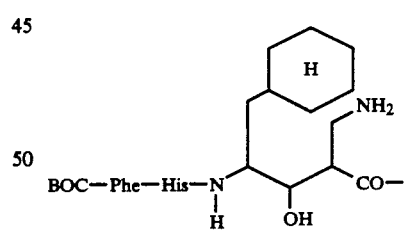

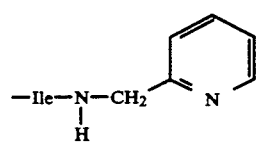

or a physiologically acceptable salt thereof.

5. A compound according to claim 1, wherein such compound is N-[2-aminomethyl-4-Boc-prolinyl-phenylalanyl-2-histidyl-amino-5-cyclohexyl-3-hydroxypentanoyl]-2-isoleucine N-(pyridyl-2-yl-methyl)-amide of the formula

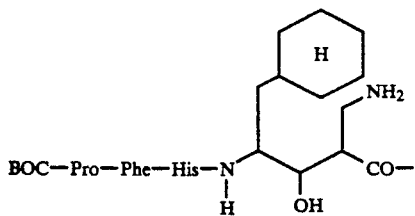

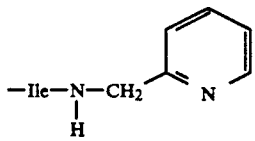

or a physiologically acceptable salt thereof.

6. A compound according to claim 1, wherein such compound is N-[2-aminomethyl-4-Boc-phenylalanyl-histidylamino-3-hydroxy-6-methylheptanoyl]-isoleucine N-(pyrid-2-yl-methyl)-amide of the formula

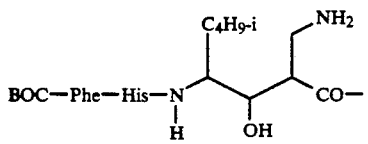

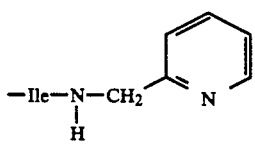

or a physiologically acceptable salt thereof.

7. A compound according to claim 1, wherein such compound is N-[2-aminomethyl-4-Boc-prolinyl-phenylalanylhistidyl-amino-3-hydroxy-6-methylheptanoyl]-isoleucine N-(pyrid-2-yl-methyl)-amide of the formula

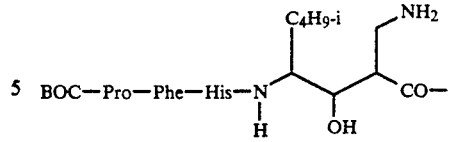

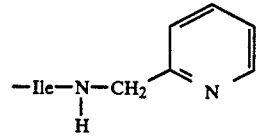

or a physiologically acceptable salt thereof.

8. A renin-inhibiting composition comprising a renin-inhibiting effective amount of a compound or salt according to claim 1 and a pharmacologically acceptable diluent.

9. A unit dose of a composition according to claim 1 in the form of a tablet, capsule or ampoule.

10. A method of inhibiting renin in a patient in need thereof which comprises administering to such patient a renin-inhibiting composition comprising a renin-inhibiting effective amount of a compound or salt according to claim 1.

11. The method according to claim 10, wherein such compound is

N-[2-aminomethyl-4-Boc-phenylalanyl-histidyl-amino-3-hydroxy-5-phenylpentanoyl]-isoleucine N-(pyrid-2-yl-methyl)-amide, N-[2-aminomethyl-4-Boc-prolinyl-phenylalanyl-histidyl-amino-3-hydroxy-5-phenylpentanoyl]isoleucine N-(pyrid-2-yl-methyl)-amide, N-[2-aminomethyl-4-Boc-phenylalanyl-2-histidyl-amino-5-cyclohexyl-3-hydroxypentanoyl]-2-isoleucine N-(pyridyl-2-yl-methyl)-amide, N-[2-aminomethyl-4-Boc-prolinyl-phenylalanyl-2-histidyl-amino-5-cyclohexyl-3-hydroxypentanoyl]-2-isoleucine N-(pyridyl-2-yl-methyl)-amide, N-[2-aminomethyl-4-Boc-phenylalanyl-histidyl-amino-3-hydroxy-6-methylheptanoyl]-isoleucine N-(pyrid-2-yl-methyl)-amide or N-[2-aminomethyl-4-Boc-prolinyl-phenylalanyl-histidyl-amino-3-hydroxy-6-methylheptanoyl]isoleucine N-(pyrid-2-yl-methyl)-amide, or a physiologically acceptable salt thereof.

* * * * *